US009757432B2

(12) United States Patent
Kaur et al.

(10) Patent No.: US 9,757,432 B2
(45) Date of Patent: Sep. 12, 2017

(54) MATERIALS AND METHODS USEFUL FOR TREATING GLIOBLASTORNA

(71) Applicants: Ohio State Innovation Foundation, Columbus, OH (US); University of Cincinnati, Cincinnati, OH (US)

(72) Inventors: Balveen Kaur, Columbus, OH (US); Jeffrey Wojton, Columbus, OH (US); Xiaoyang Qi, Cincinnati, OH (US)

(73) Assignees: Ohio State Innovation Foundation, Columbus, OH (US); University of Cincinnati, Cincinnati, OH (US)

( * ) Notice: Subject to any disclaimer, the term of this patent is extended or adjusted under 35 U.S.C. 154(b) by 0 days.

(21) Appl. No.: 14/442,782

(22) PCT Filed: Nov. 14, 2013

(86) PCT No.: PCT/US2013/070077
§ 371 (c)(1),
(2) Date: May 14, 2015

(87) PCT Pub. No.: WO2014/078522
PCT Pub. Date: May 22, 2014

(65) Prior Publication Data
US 2015/0290300 A1 Oct. 15, 2015

Related U.S. Application Data

(60) Provisional application No. 61/726,128, filed on Nov. 14, 2012.

(51) Int. Cl.
| | | |
|---|---|---|
| C07K 14/47 | (2006.01) | |
| A61K 9/127 | (2006.01) | |
| A61K 38/18 | (2006.01) | |
| A61K 38/47 | (2006.01) | |
| A61K 38/17 | (2006.01) | |
| A61K 31/436 | (2006.01) | |
| A61K 45/06 | (2006.01) | |
| A61K 31/685 | (2006.01) | |
| A61J 1/00 | (2006.01) | |
| A61K 31/4188 | (2006.01) | |
| C12N 9/24 | (2006.01) | |
| A61K 9/00 | (2006.01) | |

(52) U.S. Cl.
CPC ............... *A61K 38/47* (2013.01); *A61J 1/00* (2013.01); *A61K 31/4188* (2013.01); *A61K 31/436* (2013.01); *A61K 31/685* (2013.01); *A61K 38/1709* (2013.01); *A61K 45/06* (2013.01); *C12N 9/2402* (2013.01); *A61K 9/0019* (2013.01); *A61K 9/1272* (2013.01)

(58) Field of Classification Search
None
See application file for complete search history.

(56) References Cited

U.S. PATENT DOCUMENTS

| 5,066,493 A * | 11/1991 | Sehgal | A61K 31/445 424/122 |
| 6,872,406 B2 * | 3/2005 | Qi | C07K 14/475 424/450 |
| 7,834,147 B2 * | 11/2010 | Qi | A61K 31/685 424/450 |
| 2004/0229799 A1 | 11/2004 | Qi | |
| 2007/0185150 A1 * | 8/2007 | Bedrosian | A61K 31/502 514/299 |
| 2009/0142267 A1 * | 6/2009 | Qi | A61K 9/0014 424/9.1 |
| 2009/0269373 A1 * | 10/2009 | Qi | A61K 31/685 424/400 |

FOREIGN PATENT DOCUMENTS

| WO | 2008144591 A1 | 11/2008 | |
| WO | 2010078916 A1 | 7/2010 | |
| WO | WO 2010132233 A1 * | 11/2010 | ........... A61K 31/436 |
| WO | 2012125486 A1 | 9/2012 | |

OTHER PUBLICATIONS

Bowie, et al. Science, vol. 247: 1306-1310, 1990.*
Lazar, et al. Mol. Cell. Biol., 8(3): 1247-1252, 1988.*
Burgess, et al. J. Cell Biol. 111: 2129-2138, 1990.*
Ngo et al., in"The Protein Folding Problem and Tediary Structure Prediction", 1994, Merz, et al. (ed.), Birkhauser, Boston, MA, pp. 433, and 492-495.*
Skolnick et al., From genes to protein structure an function: novel applications of computational approaches in the genomic era, Trends in Biotech. 18: 34-39, 2000.*
Acharya et al., "PLGA nanoparticles containing various anticancer agents and tumor delivery by EPR effect", Advanced Drug Delivery Reviews, 2011, vol. 63, pp. 170-183.
Atsina, "Nanoparticles for Delivery of Rapamycin to Glioblastoma and Glioblastoma-Derived Stem Cells", Yale Medicine Thesis Digital Library, 2012, pp. 1-2, http://elischolar.library.yale.edu/ymtd1/1685/ accessed Jun. 7, 2016.
European Search Report, Application No. 13854919, dated Jun. 7, 2016.
PCT International Search Report and Written Opinion, Application No. PCT/US2013/070077, dated Feb. 24, 2014.
Wojton et al., "Lab-Experimental (Pre-Clinical) Therapeutics and Pharmacology", Neuro-Oncology, 2012, vol. 14, No. 6, pp. vi25-vi37.

(Continued)

*Primary Examiner* — Hong Sang
(74) *Attorney, Agent, or Firm* — MacMillan, Sobanski & Todd, LLC

(57) ABSTRACT

The present invention provides compositions and methods useful for treating cancers such as glioblastoma. SapC-DOPS was found to be synergistically effective at inducing cell death when administered in conjunction with rapamycin. SapC-DOPS/rapamycin combination therapy allows physicians to give lower doses of each drug and achieve better therapeutic efficacy. The compositions also allow for less toxicity and fewer off-target effects. Related methods and materials are also provided herein.

4 Claims, 14 Drawing Sheets
(11 of 14 Drawing Sheet(s) Filed in Color)

(56) References Cited

OTHER PUBLICATIONS

Wojton et al., "SapC-DOPS has antitumor efficacy in glioblastoma through the induction autophagy-associated cell death", 2013, pp. 1-2, https://kb.osu.edu/dspace/handle/1811/54416 accessed Jun. 7, 2016, Abstract only.
Wojton et al., "SapC-DOPS induces lethal mitophagy in glioblastoma", 2013 vol. 73, No. 8, p. 2169, Abstract only.

* cited by examiner

MATERIALS AND METHODS USEFUL FOR TREATING GLIOBLASTORNA

CROSS REFERENCE TO RELATED APPLICATIONS

This application claims priority to PCT application No. PCT/US2013/0070077 filed Nov. 14, 2014 which claims the benefit of U.S. Provisional Application 61/726,128, filed Nov. 14, 2012, the disclosure of which is expressly incorporated by reference.

STATEMENT REGARDING FEDERALLY SPONSORED RESEARCH

This invention was made with no government support. The government has no rights in the invention.

SEQUENCE LISTING

The Sequence Listing, filed electronically and identified as SEQ_LIST_OSIF-2013-102.txt, was created on Nov. 12, 2013, is 5,548 in size, and is hereby incorporated by reference.

```
                                                           SEQ ID NO: 1
Met Tyr Ala Leu Phe Leu Leu Ala Ser Leu Leu Gly Ale Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
            85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Glu Glu Met Ser Arg Pro
            115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 150

Gln Leu Asp Met Thr Glu Val Val Ala Pro Phe Met Ala Asn Ile Pro
            165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
            195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240

Cys Lys Asn Tyr Ile Ser Gln Thr Her Glu Ile Ala Ile Gln Met Met
            245                 250                 255
```

```
Met His Met Gln Pro Lys Glu Ile Cys Ala Leu Val Gly Phe Cys Asp
            260                 265                 270
Glu Val Lys Glu Met Pro Met Gln Thr Leu Val Pro Ala Lys Val Ala
            275                 280                 285
Ser Lys Asn Val Ile Pro Ala Leu Glu Leu Val Glu Pro Ile Lys Lys
            290                 295                 300
His Glu Val Pro Ala Lys Ser Asp Val Tyr Cys Glu Val Cys Glu Phe
305                 310                 315                 320
Leu Val Lys Glu Val Thr Lys Keu Ile Asp Asn Asn Lys Thr Glu Lys
            325                 330                 335
Glu Ile Leu Asp Ala Phe Asp Lys Met Cys Ser Lys Leu Pro Lys Ser
            340                 345                 350
Leu Ser Glu Glu Cys Gln Glu Val Val Asp Thr Tyr Gly Ser Ser Ile
            355                 360                 365
Leu Ser Ile Leu Leu Gln Glu Val Ser Pro Gln Leu Val Cys Ser Met
            370                 375                 380
Leu His Leu Cys Ser Gly Thr Arg Leu Pro Ala Leu Thr Val His Val
385                 390                 395                 400
Thr Gln Pro Lys Asp Gly Gly Phe Cys Glu Val Cys Lys Lys Leu Val
            405                 410                 415
Gly Tyr Leu Asp Arg Asn Leu Glu Lys Asn Ser Thr Lys Gln Glu Ile
            420                 425                 430
Leu Ala Ala Lys Glu Lys Gly Cys Ser Phe Leu Pro Asp Pro Tyr Gln
            435                 440                 445
Lys Gln Cys Asp Gln Phe Cal Ala Gln Tyr Glu Pro Val Leu Ile Glu
            450                 455                 460
Ile Leu Val Glu Val Met Asp Pro Ser Phe Val Cys Leu Lys Ile Gly
465                 470                 475                 480
Ala Cys Pro Ser Ala His Lys Pro Leu Leu Gly Thr Glu Lys Cys Ile
            485                 490                 495
Trp Gly Pro Ser Tyr Trp Cys Gln Asn Thr Glu Thr Ala Ala Gln Cys
            500                 505                 510
Asn Ala Val Glu His Cys Lys Arg His Val Trp Asn
            515                 520

SEQ ID NO: 2
Ser Asp Val Tyr Cys Glu Val Cys Glu Phe Leu Val Lys Glu Val Thr
1               5                   10                  15
Lys Leu Ile Asp Asn Asn Lys Thr Glu Lys Glu Ile Leu Asp Ala Phe
            20                  25                  30
Asp Lys Met Cys Ser Lys Ley Pro Cys Ser Leu Ser Glu Glu Cys Gln
            35                  40                  45
```

```
Glu Val Val Asp Thr Tyr Gly Ser Ser Ile Leu Ser Ile Leu Leu Glu
 50                  55                  60

Glu Val Ser Pro Glu Leu Val Cys Ser Met Leu His Leu Cys Ser Gly
 65                  70                  75                  80
```

BACKGROUND OF THE INVENTION

Glioblastoma is the most common primary CNS malignant neoplasm in adults, and accounts for nearly 75% of the cases. Although there has been steady progress in their treatment due to improvements in neuro-imaging, microsurgery, and radiation, glioblastomas remain incurable. The average life expectancy is less than one year from diagnosis, and the five-year survival rate following aggressive therapy, including gross tumor resection, is less than 10%. Glioblastomas cause death due to rapid, aggressive, and infiltrative growth in the brain. The infiltrative growth pattern is responsible for the un-resectable nature of these tumors. Glioblastomas are also relatively resistant to radiation and chemotherapy, and therefore post-treatment recurrence rates are high. In addition, the immune response to the neoplastic cells is mainly ineffective in completely eradicating residual neoplastic cells following resection and radiation therapy.

One problem in treating glioblastoma is the tumor's protection behind the blood-brain tumor barrier (BBTB). A significant obstacle in the development of therapeutics for glioblastoma is the inability of systemic therapies to efficiently cross the BBTB. Saposin C (SapC) is a sphingolipid-activating protein that functions to catabolize glycosphingolipids. SapC-DOPS forms stable nanovesicles which can efficiently cross the blood-brain tumor barrier and fuse with GBM cells inducing cell death.

Rapamycin is a macrolide antibiotic produced by *Streptomyces hygroscopicus*, which was discovered first for its properties as an antifungal agent. *Streptomyces hygroscopicus* has also been implicated as a cancer agent.

There remains a need in the art for new therapeutics for the treatment of glioblastoma.

SUMMARY OF THE INVENTION

The present invention provides methods to induce cell death in at least one cancer cell, comprising: a.) administering a SapC-DOPS composition to at least one cancer cell; and b.) administering an mTOR inhibitor to the at least one cancer cell and inducing cell death in the at least one cancer cell. The SapC-DOPS composition comprises a phospholipid, an isolated saposin C-related polypeptide, wherein the polypeptide comprises an amino acid sequence at least 75% identical to the entire length of SEQ ID NO: 2, and a pharmaceutically acceptable carrier, wherein the phospholipid forms a nanovesicle incorporating the polypeptide. In certain embodiments, the polypeptide comprises an amino acid sequence at least 85% identical to the entire length of SEQ ID NO: 2. In certain embodiments, the polypeptide comprises an amino acid sequence at least 95% identical to the entire length of SEQ ID NO: 2. In certain embodiments, the polypeptide comprises an amino acid sequence at least 99% identical to the entire length of SEQ ID NO: 2. In certain embodiments, the polypeptide comprises the amino acid sequence SDVYCEVCEFLVKEVTKLIDNNK-TEKEILDAFDKMCSKLPKSLSEECQEVVDTYGSSIL-SILLEEV SPELVCSMLHLCSG [SEQ ID NO: 2].

In certain embodiments, the phospholipid is selected from the group consisting of: dioleoylphosphatidylserine (DOPS); phosphatidic acid; phosphatidylethanolamine; phosphatidylcholine; phosphatidylserine; phosphoinositides such as phosphatidylinositol, phosphatidylinositol phosphate, phosphatidylinositol biphosphate, or phosphatidylinositol triphosphate; phosphatidylglycerol; cardiolipin; sphingomyelin; dimyristoylphosphatidylcholine (DMPC); phosphatidylcholine (DPPC); hydrogenated soy phosphatidylcholine (HSPC); lysophospholipids; dipalmitoyl phosphatidylserine (DPPS); distearoyl phosphatidylserine (DSPS); phosphatidyl lycerol; dipalmitoyl phosphatidylglycerol (DPPG); distearoyl phosphatidylglycerol (DSPG); phosphatidylinositol (DPPI); distearoyl phosphatidylinositol (DSPI); and combinations thereof. In certain embodiments, the phospholipid consists essentially of dioleoylphosphatidylserine (DOPS).

In certain embodiments, the mTOR inhibitor comprises a rapamycin compound. In certain embodiments, the rapamycin compound is selected from the group consisting of: (3S,6R,7E,9R,10R,12R,14S,15E,17E,19E,21 S,23S,26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]oxaazacyclohentriacontine-1,5,11,28,29(4H,6H,31H)-pentone, 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxyl)ethoxycarbonylmethyl-rapamycin, 40-O-(3-Hydroxyl)propyl-rapamycin, 40-O-(6-Hydroxy)hexyl-rapamycin, 40-O-[2-(2-Hydroxyl)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-(2-N-lmidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxyl)ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin), 40-O-[2-(4',5'-Dicarboethoxy-r,2',3'-triazol-1'-yl)-ethyl]-rapamycin, 42-deoxy-42-(1H-tetrazol-1-yl)-, (42S)-rapamycin (Zotarolimus), 42-[3-hydroxy-2-(hydroxymethyl)-2-methylpropanoate]rapamycin (temsirolimus), and tacrolimus.

In certain embodiments, the cancer is glioblastoma. In certain embodiments, the method ameliorates at least one symptom of glioblastoma in a mammal selected from the group consisting of: mouse; rat; dog; cat; monkey; and human.

In certain embodiments, the method further comprises conducting a therapy prior to or after the method, wherein the therapy is selected from the group consisting of: surgery, radiation, chemotherapy, gene therapy, alternating electrical fields, ketogenic diet, emozolomide, bevadizumab, APG101, siRNA, and stem cells. In certain embodiments, the therapy consists essentially of temozolomide.

In certain embodiments, the SapC-DOPS composition is administered simultaneously with the rapamycin. In certain embodiments, the method further comprises the step of waiting a period of time between administering the SapC-DOPS composition and administering the rapamycin compound.

In certain embodiments, the method further comprises administering an anticancer agent to the at least one cancer cell, wherein the anticancer agent is selected from the group consisting of: chemotherapeutic agents; cytotoxins; antimetabolites; alkylating agents; protein kinase inhibitors; anthracyclines; antibiotics; antimitotic agents; corticosteroids; radiopharmaceuticals; cytokines; enzymes; interferons; krestin; lentinan; sizofiran; picibanil; ubenimex; acitretin; fenretinide; thalidomide; zoledronic acid; angiostatin; aplidine; cilengtide; combretastatin A-4; endostatin; halofuginone; rebimastat; removab; Revlimid; squalamine; ukrain; Vitaxin; cisplatin; carboplatin; nedaplatin; oxaliplatin; camptothecin derivatives; compounds or chelates that include radionuclides; filgrastim; lentinan; sizofilan; TheraCys; ubenimex; WF-10; aldesleukin; alemtuzumab; BAM-002; dacarbazine; daclizumab; denileukin; gemtuzumab ozoganmicin; ibritumomab; imiquimod; lenograstim; lentinan; Corixa; molgramostim; OncoVAX-CL; sargramostim; tasonermin; tecleukin; thymalasin; tositumomab; Virulizin; Z-100; epratuzumab; mitumomab; oregovomab; pemtumomab; Provenge; alitretinoin; ampligen; atrasentan bexarotene; bortczomib; Bosentan; calcitriol; exisulind; finasteride fotemustine; ibandronic acid; miltefosine; mitoxantrone; 1-asparaginase; procarbazine; dacarbazine; hydroxycarbamide; pegaspargase; pentostatin; tazarotne; Telcyta; Velcade; tretinoinor; macitentan; carmustine; (R)-7-Acetyl-5-(4-aminophenyl)-8,9-dihydro-8-methyl-7H—I, 3-dioxolo[4,5-H][2,3]benzodiazepine; and combinations thereof.

Further provided herein is a composition of matter comprising an anionic phospholipid; a polypeptide derived from Saposin C, wherein the anionic phospholipid incorporates the polypeptide in a nanovesicle; a mTOR inhibitor; and a pharmaceutically acceptable carrier. In certain embodiments, the mTOR inhibitor is selected from the group consisting of: rapamycin; temsirolimus; everolimus; deferolimus; and combinations thereof. In certain embodiments, the mTOR inhibitor consists essentially of rapamycin. In certain embodiments, the molar ratio of the polypeptide to the phospholipid is in the range of from about 1:1 to about 1:50. In certain embodiments, the molar ratio of the polypeptide to the phospholipid is in the range of from about 1:1:to about 1:10. In certain embodiments, the mass ratio of the polypeptide to the phospholipid is in the range of from about 15:1 to about 3:10.

In certain embodiments, the polypeptide comprises at least 25 contiguous amino acids of SEQ ID NO: 2. In certain embodiments, the polypeptide comprises an amino acid sequence at least 85% identical to the entire length of SEQ ID NO: 2. In certain embodiments, the polypeptide comprises an amino acid sequence at least 95% identical to the entire length of SEQ ID NO: 2. In certain embodiments, the polypeptide comprises an amino acid sequence at least 99% identical to the entire length of SEQ ID NO: 2. In certain embodiments, the polypeptide comprises the amino acid sequence

```
[SEQ ID NO: 2]
SDVYCEVCEFLVKEVTKLIDNNKTEKEILDAFDKMCSKLPKSLSEECQEV
VDTYGSSILSILLEEVSPELVCSMLHLCSG.
```

In certain embodiments, the nanovesicle has a diameter in the range of from about 10 nm to about 800 nm. In certain embodiments, the mass ratio of the polypeptide to the phospholipid is approximately 5:1. In certain embodiments, the mass ratio of the polypeptide to the phospholipid is approximately 15:7.

Further provided herein are cells comprising the composition of matter previously described. In certain embodiments, the cell is selected from the group consisting of: bacteria; yeast; mouse cell; rat cell, cat cell, dog cell, monkey cell, human cell, archael cell, insect cell, plan cell, algal cell, fungal cell, amphibian cell, reptile cell, worm cell, and animal cell culture lines.

Further provided herein is a composition resulting by ingestion in the composition previously described.

Further provided herein is a method of treating cancer in a human in need of such treatment, comprising administering an effective amount of the composition previously described to the human and treating cancer. In certain embodiments, the cancer is glioblastoma.

Further provided herein is a kit for preparing a cancer treatment comprising a first container housing a saposin C-related polypeptide; a second container housing a mTOR inhibitor; and a third container housing a pharmaceutically acceptable carrier, diluent, or excipient. In certain embodiments, the saposin C-related polypeptide comprises an amino acid sequence at least 75% identical to the entire length of SEQ ID NO: 2. In certain embodiments, the mTOR inhibitor comprises a rapamycin compound.

Also provided are methods to ameliorate at least one symptom of glioblastoma in a mammal, comprising: a.) administering a pharmaceutically-effective amount of at least one P13K/mTOR dual inhibitor to a patient with glioblastoma and in need of symptom amelioration, and b.) ameliorating at least one symptom of glioblastoma. In certain embodiments, the P13K/mTOR dual inhibitor is selected from the group consisting of: NVP-BEZ235; BGT226; SF1126; PKI-587; INK128; AZD8055; and AZD2014.

Also provided are methods to ameliorate at least one symptom of glioblastoma in a mammal, comprising: a.) administering a pharmaceutically-effective amount of at least one P13K inhibitor and at least one mTOR inhibitor to a patient with glioblastoma and in need of symptom amelioration, and b.) ameliorating at least one symptom of glioblastoma. In certain embodiments, the P13K inhibitor is selected from the group consisting of: NVP-BEZ235; BGT226; SF1126; PKI-587; INK128; AZD8055; and AZD2014. In certain embodiments, the mTOR inhibitor is rapamycin or an analog thereof. In certain embodiments, the mTOR inhibitor is selected from the group consisting of: rapamycin; sirolimus; temsirolimus; everolimus; and deferolimus.

Also provided are such methods, wherein the method induces lethal mitophagy or anti-angiogenesis.

Also provided are such methods, wherein mammal is selected from the group consisting of: mouse; rat; cat; dog; monkey; and human.

The present disclosure provides compositions comprising at least one PI3K inhibitor and at least one mTOR inhibitor, or a pharmaceutically-acceptable formulation thereof. In certain embodiments, the P13K inhibitor is selected from the group consisting of: SapC-DOPS; NVP-BEZ235; BGT226; SF1126; PKI-587; INK128; AZD8055; and AZD2014. In certain embodiments, the mTOR inhibitor is rapamycin or an analog thereof. In certain embodiments, the mTOR inhibitor is selected from the group consisting of: rapamycin; sirolimus; temsirolimus; everolimus; and deferolimus.

The present invention provides compositions comprising at least one PI3K/mTOR dual inhibitor and at least one mTOR inhibitor, or a pharmaceutically-acceptable formulation thereof.

Also provided are compositions of matter herein, wherein the P13K/mTOR dual inhibitor is selected from the group consisting of: NVP-BEZ235; BGT226; SF1126; PKI-587; INK128; AZD8055; and AZD2014.

Also provided are compositions of matter herein, wherein the mTOR inhibitor is selected from the group consisting of: rapamycin; sirolimus; temsirolimus; everolimus; and deferolimus.

Also provided are cells comprising compositions of matter herein. In certain embodiments, the cells are selected from the group consisting of: bacteria; yeast; mouse cell; rat cell; cat cell; dog cell; monkey cell; human cell; archael cell; insect cell; plant cell; algal cell; fungal cell; amphibian cell; reptile cell; worm cell; and animal cell culture lines.

Also provided are organisms comprising a composition herein. In certain embodiments, the organisms are selected from the group consisting of: bacteria archaea, yeast; mouse; rat; cat; dog; monkey; human; algae; plants; fungus; insects; amphibians; reptiles; worms; and animal cell culture lines.

Also provided are drug discovery assays comprising a composition herein.

Also provided are toxicity assays comprising a composition herein.

Also provided are safety assays comprising a composition herein.

Also provided are kits comprising a composition herein.

Also provided are compositions or methods herein, wherein the SapC-DOPS comprises a phospholipid incorporating the polypeptide in a nanovesicle, wherein the polypeptide retains plasma membrane affinity, and wherein the nanovesicle incorporating the polypeptide exhibits anti-tumor activity.

Also provided are such compositions or methods, wherein the molar ratio of the polypeptide to the phospholipid is in the range from about 1:1 to about 1:10.

Also provided are such compositions or methods, wherein the polypeptide comprises at least 25 contiguous amino acids of SEQ ID NO: 2.

Also provided are such compositions or methods, wherein the mass ratio of the polypeptide to the phospholipid is in the range from about 15:1 to about 3:10.

Also provided are such compositions or methods, comprising a nanovesicle prepared by (a) preparing a composition that comprises (i) a dried inner leaflet component, wherein the inner leaflet component is a phospholipid, wherein the phospholipid is dioleoylphosphatidylserine (DOPS) and (ii) a dried and isolated prosaposin-related polypeptide; wherein the polypeptide has an amino acid sequence selected from the group consisting of the amino acid sequence set forth in SEQ ID NO: 1, the amino acid sequence that is at least 95 percent identical to the entire length of SEQ ID NO: 1, the amino acid sequence set forth in SEQ ID NO: 2, and the amino acid sequence that is at least 95 percent identical to the entire length of SEQ ID NO:2; wherein the molar ratio of the polypeptide to the dioleoylphosphatidylserine in the composition is in the range from 1:1 to 1:25; in a pharmaceutically acceptable carrier; (b) treating the composition to form a nanovesicle; wherein the nanovesicle formed has a diameter in the range 10 to 800 nm; and wherein the composition is capable of inducing apoptosis in hyper-proliferating cells, wherein the hyper-proliferating cells are cancer cells.

Also provided are such compositions or methods, wherein the mass ratio of the polypeptide to the dioleoylphosphatidylserine is approximately 5:1.

Also provided are such compositions or methods, wherein the mass ratio of the polypeptide to the dioleoylphosphatidylserine is approximately 15:7.

Also provided are such compositions or methods, wherein the mass ratio of the polypeptide to the dioleoylphosphatidylserine is in the range from about 15:1 to about 3:10.

Also provided are such compositions or methods, comprising approximately 10 µM polypeptide and approximately 30 µM dioleoylphosphatidylserine.

Also provided are such compositions or methods, comprising approximately 10 µM polypeptide and approximately 70 µM dioleoylphosphatidylserine.

Also provided are such compositions or methods, wherein the SapC-DOPS consists essentially of an anionic phospholipid nanovesicle consisting essentially of dioleoylphosphatidylserine (DOPS) embedded with a biologically active saposin C-related polypeptide, wherein the polypeptide comprises an amino acid sequence that has at least 75% sequence identity to the amino acid sequence of the entire length of SEQ ID NO:2; and a pharmaceutically acceptable carrier; wherein the phospholipid nanovesicle exhibits anti-tumor activity.

Also provided are such compositions or methods, wherein the molar ratio of the polypeptide to the phospholipid is in the range from about 1:1 to about 1:50.

Also provided are such compositions or methods, wherein the molar ratio of the polypeptide to the phospholipid is in the range from about 1:1 to about 1:10.

The present invention comprises compositions comprising SapC-DOPS and rapamycin, or a pharmaceutically-acceptable formulation thereof.

Also provided are methods to treat glioblastoma in a human in need of treatment, comprising administering a SapC-DOPS and rapamycin, or a pharmaceutically-acceptable formulation thereof.

Also provided are methods to induce lethal mitophagy in at least one glioblastoma cell, comprising: a.) administering SapC-DOPS to at least one glioblastoma cell, and b.) inducing lethal mitophagy in at least one glioblastoma cell.

Various aspects of this invention will become apparent to those skilled in the art from the following detailed description of the preferred embodiment, when read in light of the accompanying figures.

BRIEF DESCRIPTION OF THE FIGURES

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

DETAILED DESCRIPTION OF THE INVENTION

Figure 1:
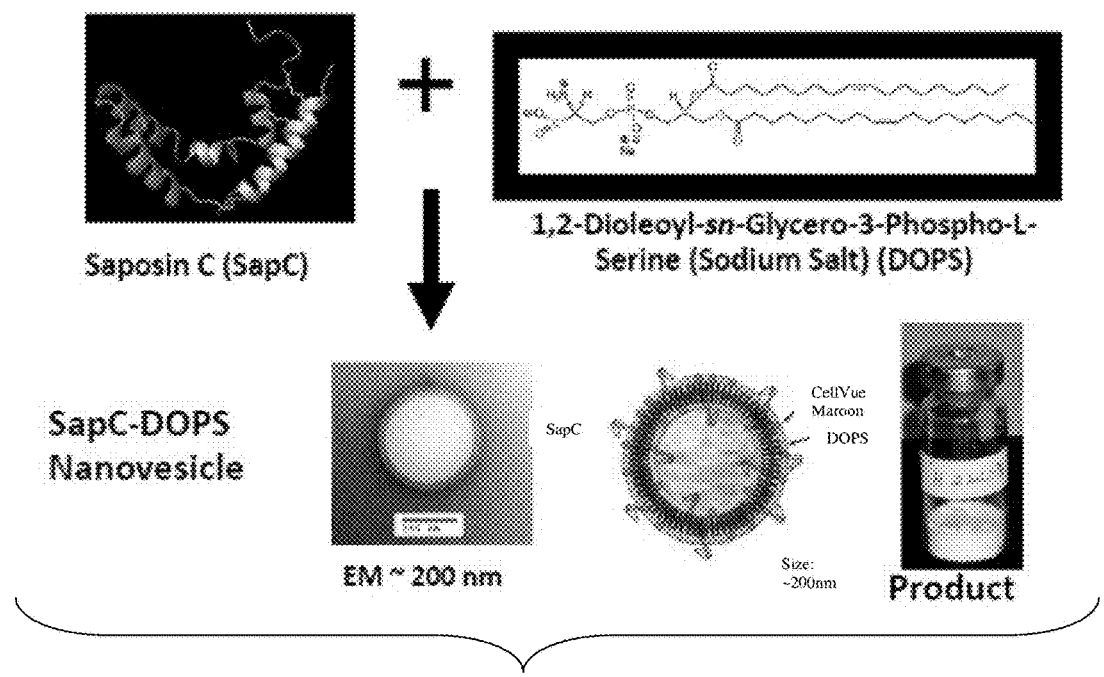
FIG. 1: A schematic of the SapC-DOPS structure.

For convenience, certain terms employed in the specification, examples, and appended claims are collected here, before further description of the invention. These definitions should be read in light of the remainder of the disclosure and understood as by a person of skill in the art. Unless defined otherwise, all technical and scientific terms used herein have the same meaning as commonly understood by a person of ordinary skill in the art.

"Patient" or "subject" refers to animals, including mammals, preferably humans.

As used herein, "pharmaceutical agent or drug" refers to any chemical or biological material, compound, or composition capable of inducing a desired therapeutic effect when properly administered to a patient. Some drugs are sold in an inactive form that is converted in vivo into a metabolite with pharmaceutical activity. For purposes of the present invention, the terms "pharmaceutical agent" and "drug" encompass both the inactive drug and the active metabolite.

The term "angiogenesis" refers to the growth of new blood vessels.

The phrase "pharmaceutically or therapeutically effective dose or amount" refers to a dosage level sufficient to induce a desired biological result. That result may be the delivery of a pharmaceutical agent, alleviation of the signs, symptoms or causes of a disease or any other desired alteration of a biological system and the precise amount of the active depends on the physical condition of the patient, progression of the illness being treated etc.

As used herein, the term "saposin" refers to the family of prosaposin-derived proteins and polypeptides, including, but not limited to, naturally occurring saposins A, B, C, and D, as well as synthetic saposin-derived proteins and peptides and peptide analogs showing fusogenic activity. The saposin C and polypeptides derived therefrom may be used in certain embodiments of the invention.

The term "SapC analogs" refers to substitutions or alterations in the amino acid sequences of the peptides disclosed herein, which substitutions or alterations do not adversely affect the fusogenic properties of the peptides. Thus, an analog might comprise a peptide having a substantially identical amino acid sequence to a peptide provided herein, such as SEQ ID NO:1, or SEQ ID NO:2, and in which one or more amino acid residues have been conservatively substituted with chemically similar amino acids. Examples of conservative substitutions include the substitution of a non-polar (hydrophobic) residue such as isoleucine, valine, leucine, or methionine for another. Likewise, the present invention contemplates the substitution of one polar (hydrophilic) residue such as between arginine and lysine, between glutamine and asparagine, and between glycine and serine. Additionally, the substitution of a basic residue such as lysine, arginine, or histidine for another, or the substitution of one acidic residue such as aspartic acid or glutamic acid for another, is also contemplated.

The term "variant" SapC protein refers to a protein derived from the native protein by deletion (so-called truncation) or addition of one or more amino acids to the N-terminal and/or C-terminal end of the native protein; deletion or addition of one or more amino acids at one or more sites in the native protein; substitution of one or more amino acids at one or more sites in the native protein; or synthetically-produced polypeptides having such an amino acid sequence. Variant proteins encompassed by the present disclosure are biologically active, meaning they continue to possess the desired biological activity of the native protein. By way of non-limiting example, such biological activity may include plasma membrane affinity as described herein. Such variants may result from, for example, genetic polymorphism or from human manipulation. Biologically active variants of a native prosaposin protein of the present disclosure have at least about 75%, 80%, 85%, preferably at least about 90%, 91%, 92%, 93%, 94%, 95%, 96%, 97%, or more preferably at least about 98% or 99% sequence identity to the amino acid sequence for the native protein. Sequence identity can be determined by sequence alignment programs described elsewhere using default parameters. A biologically active variant of a protein of the present disclosure may differ from that protein by as few as 1-15 amino acid residues, as few as 1-10, such as 6-10, as few as 5, as few as 4, 3, 2, or even 1 amino acid residue.

The present disclosure provides compositions and methods useful for treating cancer, such as glioblastoma. Saposin C ("SapC") dioleoylphosphatidylserine ("DOPS") and modifications, variants, analogs, and formulations are known. U.S. Pat. No. 7,834,147 describes many such compositions and formulations, and such compositions and formulations are useful in the present disclosure. U.S. Pat. No. 7,834,147 is hereby incorporated by reference. SapC-DOPS, especially the therapeutic licensed by Bexion Pharmaceuticals, was found by the inventors to be synergistically effective at inducing lethal mitophagy when administered with rapamycin.

Thus, provided herein are compositions and methods for treating cancers, such as glioblastoma, involving the combination of a SapC-DOPS composition (or a SapC-DOPS analog or variant) and a rapamycin compound (such as rapamycin, a rapamycin analog, or a rapamycin derivative). In certain embodiments, the SapC-DOPS composition comprises a phospholipid, a saposin C-related polypeptide, and a pharmaceutically acceptable carrier, wherein the phospholipid forms a nanovesicle incorporating the polypeptide. In certain embodiments, the saposin C-related peptide has the amino acid sequence SDVYCEVCEFLVKEVTKLIDNNK-TEKEILDAFDKMCSKLPKSLSEECQEVVDTYGSSIL-SILLEEV SPELVCSMLHLCSG [SEQ ID NO: 2]. In certain embodiments, the saposin C-related peptide has an amino acid sequence having at least 75% identity to SEQ ID NO:2. In certain embodiments, the saposin C-related peptide has at least 25 contiguous amino acids of SEQ ID NO:2.

It is to be understood that the SapC-DOPS compositions presently disclosed include a phospholipid, which is generally described herein for illustrative purposes as being DOPS, but many other phospholipids are possible. Suitable phospholipids include, but are not limited to: DOPS; phosphatidic acid; phosphatidylethanolamine; phosphatidylcholine; phosphatidylserine; phosphoinositides such as phosphatidylinositol, phosphatidylinositol phosphate, phosphatidylinositol biphosphate, or phosphatidylinositol triphosphate; phosphatidylglycerol; cardiolipin; sphingomyelin; dimyristoylphosphatidylcholine (DMPC); dipalmitoyl phosphatidylcholine (DPPC); hydrogenated soy phosphatidylcholine (HSPC); lysophospholipids; dipalmitoyl phosphatidylserine (DPPS); distearoyl phosphatidylserine (DSPS); phosphatidyl lycerol; dipalmitoyl phosphatidylglycerol (DPPG); distearoyl phosphatidylglycerol (DSPG); dipalmitoyl phosphatidylinositol (DPPI); distearoyl phosphatidylinositol (DSPI) or combinations thereof. In particular embodiments, the phospholipid is an anionic phospholipid. In particular embodiments, the phospholipid consists essentially of DOPS.

Figure 2:
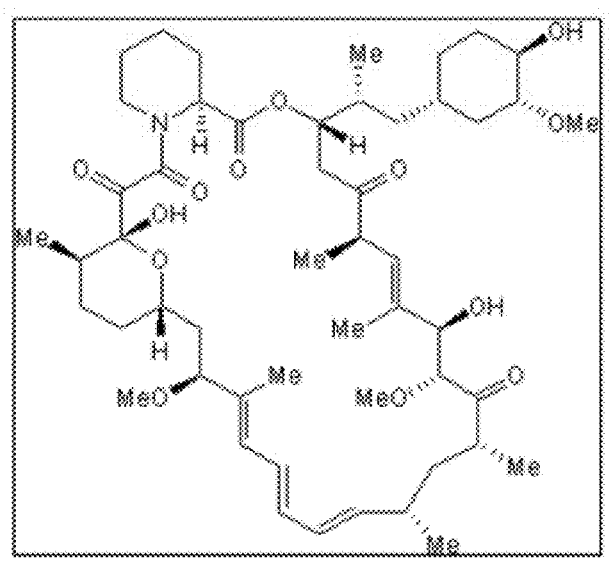
FIG. 2: A schematic of the rapamycin structure.

Rapamycin, its preparation, and its antibiotic activity, are described in U.S. Pat. No. 3,929,992, issued Dec. 30, 1975 to Surendra Sehgal et al. The chemical structure of rapamycin is depicted in FIG. 2. In 1977, Martel, R. R. et al. reported on immunosuppressive properties of rapamycin against experimental allergic encephalitis and adjuvant arthritis in the Canadian Journal of Physiological Pharmacology, 55, 48-51 (1977) (incorporated by reference). In 1989, Calne, R. Y. et al. in Lancet, 1989, no. 2, p. 227 and Morris, R. E. and Meiser, B. M. in Medicinal Science Research, 1989, No. 17, P. 609-10, separately reported on the effectiveness of rapamycin in inhibiting rejection in vivo in allograft transplantation. The immunosuppressive and rejection-inhibiting properties of rapamycin have also been described, and clinical investigations have begun for the use of rapamycin in inhibiting rejection in transplantation in man.

Certain rapamycin analogs are described and included herein. Suitable rapamycin analogs include, but are not limited to, substituted rapamycin such as a 40-O-substituted rapamycin, described in U.S. Pat. No. 5,258,389, WO 94/09010, WO 92/05179, U.S. Pat. No. 5,118,677, U.S. Pat. No. 5,118,678, U.S. Pat. No. 5,100,883, U.S. Pat. No. 5,151,413, U.S. Pat. No. 5,120,842, WO 93/11130, WO 94/02136, WO 94/02485, and WO 95/14023, all of which are incorporated herein by reference; a 16-O-substituted rapamycin, disclosed in WO 94/02136, WO 95/16691, and WO 96/41807, the contents of which are incorporated herein by reference; or a 32-hydrogenated rapamycin, described in WO 96/41807 and U.S. Pat. No. 5,256,790, incorporated herein by reference.

As used herein, the term "rapamycin compound" includes rapamycin and all analogs, derivatives, and conjugates that bind to FKBP12, and other immunophilins that possesses the same pharmacologic properties as rapamycin, including inhibition of the target of rapamycin (TOR). Sirolimus is a rapamycin also know as (3S,6R,7E,9R,10R,12R,14S,15E, 17E,19E,21 S,23S,26R,27R,34aS)-9,10,12,13,14,21,22,23, 24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1.4] oxaazacyclohentriacontine-1,5,11,28,29(4H,6H,31H)-pentone. Other analogs, derivatives, and conjugates that may be processed into a substantially solvent-free amorphous solid include, but are not limited to, 40-O-(2-Hydroxyethyl) rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxyl)ethoxycarbonylmethyl-rapamycin, 40-O-(3-Hydroxyl)propyl-rapamycin, 40-O-(6-Hydroxyl)hexyl-rapamycin, 40-O-[2-(2-Hydroxyl) ethoxy]ethyl-rapamycin, 40-O-[(3S)-2,2-Dimethyldioxolan-3-yl]methyl-rapamycin, 40-O-[(2S)-2,3-Dihydroxy-prop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-(2-N-lmidazolylacetoxy)ethyl-rapamycin, 40-O-[2-(N-Methyl-N'-piperazinyl) acetoxy]ethyl-rapamycin, 39-O-Desmethyl-39,40-O,O-ethylene-rapamycin, (26R)-26-Dihydro-40-O-(2-hydroxyl) ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin), 40-O-[2-(4',5'-Dicarboethoxy-r,2',3'-triazol-1'-yl)-ethyl]-rapamycin, 42-deoxy-42-(1H-tetrazol-1-yl)-, (42S)-rapamycin (Zotarolimus), 42-[3-hydroxy-2-(hydroxymethyl)-2-methylpropanoate]rapamycin (temsirolimus), and tacrolimus.

Amorphous rapamycin-like compounds, such as sirolimus, may be prepared or processed in a manner such that it is in a stable form that may be administered in any number of ways. For example, the sirolimus may be administered orally, parenterally, intravascularly, intranasally, intrabronchially, transdermal, rectally, or via a coated medical device such as a stent coated with sirolimus.

The synergistic interactions between the present compositions and methods allow physicians to give lower doses of each drug and achieve better therapeutic efficacy. The compositions and methods also allow for less toxicity and off-target effects. In certain embodiments, the compositions can efficiently cross the blood-brain tumor barrier (BBTB) and are useful for treating various cancers such as, but not limited to, glioblastoma, by inducing cell death. In certain embodiments, the compositions exert anti-angiogenesis effects by inhibiting the growth of blood vessels. In certain embodiments, the compositions induce lethal mitophagy.

The methods herein generally involve the administration of a SapC-DOPS composition and a rapamycin compound. In certain embodiments, the SapC-DOPS composition and the rapamycin compound are administered simultaneously. In certain embodiments, the SapC-DOPS composition and the rapamycin compound are administered sequentially. In particular embodiments wherein the SapC-DOPS composition and the rapamycin compound are administered sequentially, the method further comprises the step of waiting a period of time before administering the rapamycin. In certain embodiments, the sequential administration can be given over the course of cycles wherein the order of administration is varied.

In certain embodiments, the methods herein further comprise conducting a therapy prior to or after the administration of a SapC-DOPS composition and a rapamycin compound, wherein the therapy is selected from the group consisting of: surgery; radiation; chemotherapy; gene therapy; alternating electrical fields; ketogenic diet; temozolomide; bevadizumab; APG101; siRNA; and stem cells. In certain embodiments, the therapy is temozolomide. In certain embodiments, the therapy involves gene silencing through the administration of small interfering RNA (siRNA). In one non-limiting example, the siRNA target epidermal growth factor receptor (EGFR) and/or β-catenin. In another non-limiting example, the siRNA inhibit the expression of the stem cell marker Rex-1. In certain embodiments, the therapy involves administering stem cells such as GBM6-AD stem cells.

In certain embodiments, the methods further include the step of administering a conventional anticancer agent. Suitable anticancer agents for use in combination with a SapC-DOPS composition and a rapamycin compound include, but are not limited to: chemotherapeutic agents; cytotoxins; antimetabolites; alkylating agents; protein kinase inhibitors; anthracyclines; antibiotics; antimitotic agents (e.g. antitubulin agents); corticosteroids; radiopharmaceuticals; proteins such as cytokines, enzymes, or interferons; biological response modifiers such as krestin, lentinan, sizofiran, picibanil, ubenimex; anti-angiogenic compounds such as acitretin, fenretinide, thalidomide, zoledronic acid, angiostatin, aplidine, cilengtide, combretastatin A-4, endostatin, halofuginone, rebimastat, removab, Revlimid, squalamine, ukrain, or Vitaxin; platinum-coordinated compounds such as cisplatin, carboplatin, nedaplatin, or oxaliplatin; camptothecin derivatives such as camptothecin, 10-hydroxycamptothecin, 9-aminocamptothecin, irinotecan, SN-38, edotecarin, or topotecan; compounds or chelates that include radionuclides; or combinations thereof. Examples of suitable interferons include, but are not limited to interferon alpha, interferon alpha-2a, interferon, alpha-2b, interferon beta, interferon gamma-1a, interferon gamma-1b (Actimmune), interferon gamma-n1, or combinations thereof. In certain embodiments, the anticancer agent is one or more of filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, Corixa, molgramostim, OncoVAX-CL, sargramostim, tasonermin, tecleukin, thymalasin, tositumomab, Virulizin, Z-100, epratuzumab, mitumomab, oregovomab, pemtumomab (Y-muHMFGI), Provenge (Dendreon), alitretinoin, ampligen, atrasentan bexarotene, bortezomib, Bosentan, calcitriol, exisilind, finasteride, fotemustine, ibandronic acid, miltefosine, mitoxantrone, 1-asparaginase, procarbazine, dacarbazine, hydroxycarbamide, pegaspargase, pentostatin, tazarotne, Telcyta (TLK-286, Telik Inc.), Velcade (bortemazib, Millenium), tretinoinor, maceitentan, carmustine, (R)-7-Acetyl-5-(4-aminophenyl)-8,9-dihydro-8-methyl-7H—I,3-dioxolo [4,5-H][2,3]benzodiazepine; or combinations thereof. In certain embodiments, the anticancer agent comprises maciтentan in combination with a cytotoxic therapy agent such as temozolomide or paclitaxel. In certain embodiments, the anticancer agent comprises carmustine, which may or may not be in a pharmaceutical composition comprising thymosin-al as an adjuvant. In certain embodiments, the anti-cancer agent comprises (R)-7-Acetyl-5-(4-aminophenyl)-8,9-dihydro-8-methyl-7H—I,3-dioxolo[4,5-H][2,3] benzodiazepine.

As used herein, the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

An anti-tumor agent or pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, intraperitoneal, and rectal administration. Solutions or suspensions used for parenteral, intradermal, or subcutaneous application can include the following components: a sterile diluent such as water for injection, saline solution, fixed oils, polyethylene glycols, glycerin, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.), or phosphate-buffered saline (PBS). In all cases, the composition must be sterile and should be fluid to the extent that easy syringability exists. It must be stable under the conditions of manufacture and storage, and must be preserved against the contaminating action of microorganisms such as bacteria and fungi. The carrier can be a solvent or dispersion medium containing, for example, water, ethanol, a polyol (for example, glycerol, propylene glycol, liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, such as parabens, chlorobutanol, phenol, ascorbic acid, thimerosal, and the like. In many cases, it is preferable to include isotonic agents, such as sugars or polyalcohols such as mannitol, sorbitol, and sodium chloride, in the composition. Prolonged absorption of the injectable compositions can be brought about by including in the composition an agent that delays absorption, such as aluminum monostearate or gelatin.

Sterile injectable solutions can be prepared by incorporating the active compounds (e.g., a prosaposin-related polypeptide and an inner leaflet component) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches or the like can contain any of the following ingredients, or compounds of a similar nature: a binder such as microcrystalline cellulose, gum tragacanth, or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, which is incorporated herein by reference.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 µg/kg to about 15 mg/kg (e.g., 0.1 to 20 mg/kg) of an agent of the invention is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188, which is incorporated herein by reference. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

The anti-tumor or anti-cancer agents described herein can be administered transdermally. Transdermal administration typically involves the delivery of a pharmaceutical agent for percutaneous passage of the drug into the systemic circulation of the subject or patient. The skin sites include anatomic regions for transdermally administering the drug and include the forearm, abdomen, chest, back, buttock, mastoidal area, and the like.

Transdermal delivery is accomplished by exposing a source of the agent or complex to a patient's skin for an extended period of time. Transdermal patches have the added advantage of providing controlled delivery of a pharmaceutical agent to the body (see Hadgraft and Guy (eds) (1989) Transdermal Drug Delivery: Developmental Issues and Research Initiatives, Marcel Dekker, Inc.; Robinson & Lee (eds) (1987) Controlled Drug Delivery: Fundamentals and Applications, Marcel Dekker, Inc; and Kydonieus & Berner (eds) (1987) Transdermal Delivery of Drugs vols 1-3, CRC Press, incorporated herein by reference). Such dosage forms can be made by dissolving, dispersing, or otherwise incorporating the combination of saposin C related polypeptide and dioleoylphosphatidylserine (DOPS) in a proper medium, such as an elastomeric matrix material. Absorption enhancers can also be used to increase the flux of the compound across the skin. The rate of such flux can be controlled by providing a rate-controlling membrane or dispersing the agent in a polymer matrix or gel.

A variety of types of transdermal patches will find use in the methods described herein. For example, a simple adhesive patch can be prepared from a backing material and an acrylate adhesive. The pharmaceutical agent and any enhancer are formulated into the adhesive casting solution and allowed to mix thoroughly. The solution is cast directly onto the backing material and the casting solvent is evaporated in an oven, leaving an adhesive film. The release liner can be attached to complete the system.

Alternatively, a polyurethane matrix patch can be employed to deliver the agent. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast on the backing material.

A further embodiment of this invention will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer.

For passive delivery systems, the rate of release is typically controlled by a membrane placed between the reservoir and the skin, by diffusion from a monolithic device, or by the skin itself serving as a rate-controlling barrier in the delivery system (see U.S. Pat. Nos. 4,816,258; 4,927,408; 4,904,475; 4,588,580; and 4,788,062, each of which is incorporated herein by reference). The rate of drug delivery is dependent in part upon the nature of the membrane. For example, the rate of drug delivery across membranes within the body is generally higher than across dermal barriers. The rate at which the agent is delivered from the device to the membrane is most advantageously controlled by the use of rate-limiting membranes placed between the reservoir and the skin. When the skin is sufficiently permeable to the complex (that is, absorption through the skin is greater than the rate of passage through the membrane), the membrane serves to control the dosage rate experienced by the patient.

Suitable permeable membrane materials may be selected based on the desired degree of permeability, the nature of the agent, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials such as cellulose triacetate or cellulose nitrate/acetate, and hydrogels such as 2-hydroxyethylmethacrylate (HEMA).

Other items may be contained in the device, such as other pharmaceutically acceptable carriers, depending on the desired device characteristics. For example, the compositions according to this disclosure may also include one or more preservatives or bacteriostatic agents such as methyl hydroxybenzoate, propyl hydroxybenzoate, chlorocresol, benzalkonium chlorides, and the like. These pharmaceutical compositions can also contain other active ingredients such as anti-microbial agents, particularly antibiotics, anesthetics, and antipruritic agents.

Another aspect of this disclosure provides for the topical delivery of an agent or composition of the disclosure. This treatment regimen is suitable either for the systemic administration of the anti-tumor agent or for localized therapy, that is, directly to pathological or diseased tissue.

Typically, the topical formulations comprise a preparation for delivering the agent directly to the affected area comprising the complex, typically in concentrations in the range of from about 0.001% to 10%; preferably, from about 0.01 to about 10%; more preferably from about 0.1 to about 5%; and most preferably from about 1 to about 5%, together with a non-toxic, pharmaceutically acceptable topical carrier (Barry (eds). Dermatological Formulations: Percutaneous Absorption (1983) Marcel Dekker, Inc; for standard dosages of conventional pharmaceutical agents see, e.g., Physicians' Desk Reference (1992 Edition); and American Medical Association (1992) Drug Evaluations Subscriptions).

Topical preparations can be prepared by combining the agent with conventional pharmaceutical diluents and carriers commonly used in topical dry, liquid, cream, and aerosol formulations. Ointment and creams may, for example, be formulated with an aqueous or oily base with the addition of suitable thickening and/or gelling substances. Such bases may include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, wool fat, hydrogenated lanolin, beeswax, and the like. Lotions may be formulated with an aqueous or oily base and, in general, also include one or more of the following: stabilizing agents, emulsifying agents, dispersing agents, suspending agents, thickening agents, coloring agents, perfumes, and the like. Powders may be formed with the aid of any suitable base such as talc, lactose, starch, and the like. Drops may be formulated with an aqueous base or non-aqueous base also comprising one or more dispersing agents, suspending agents, solubilizing agents, and the like.

Dosage forms for the topical administration of an agent of this invention include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required.

The ointments, pastes, creams, and gels also may contain excipients, such as animal and vegetable fats, oils, waxes, paraffins, starch, tragacanth, cellulose derivatives, polyethylene glycols, silicones, bentonites, talc, and zinc oxide, or mixtures thereof. Powders and sprays can also contain excipients such as lactose, talc, aluminum hydroxide, calcium silicates, and polyamide powder, or mixtures of those substances. Sprays can additionally contain customary propellants, such as chlorofluorohydrocarbons and volatile unsubstituted hydrocarbons such as butane and propane.

The methods of the present invention are also applicable to the delivery of pharmaceutical agents through mucosal membranes such as gastrointestinal, sublingual, buccal, nasal, pulmonary, vaginal, corneal, and ocular membranes (Mackay et al. (1991) Adv. Drug Del. Rev. 7:313-338).

For delivery to the buccal or sublingual membranes, typically an oral formulation such as a lozenge, tablet, or capsule will be used. The methods of manufacture of these formulations are known in the art and include, but are not limited to, the addition of the agent to a pre-manufactured tablet; cold compression of an inert filler or a binder; and encapsulation.

Another oral formulation is one that can be applied with an adhesive such as the cellulose derivative, hydroxypropyl cellulose, to the oral mucosa, for example as described in U.S. Pat. No. 4,940,587, incorporated herein by reference. This buccal adhesive formulation, when applied to the buccal mucosa, allows for the controlled release of an agent into the mouth and through the buccal mucosa.

For delivery to the nasal and/or pulmonary membranes, typically an aerosol formulation will be employed. The term "aerosol" includes any gas-borne suspended phase of an agent of the invention which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of the agent suspended in air or other carrier gas, which may be delivered by inhalation from an inhaler device.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide in the agent (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 15 mg/kg. A therapeutically effective amount of an inner leaflet component in the agent (i.e., an effective dosage) ranges from about 0.001 to 30 mg/kg body weight, preferably from about 0.01 to about 30 mg/kg body weight, more preferably about 0.01 to about 20 mg/kg body weight, yet more preferably 0.01 to 10 mg/kg body weight, and even more preferably about 0.1 to 9 mg/kg, 0.1 to 8 mg/kg, 0.1 to 7 mg/kg, 0.1 to 6 mg/kg, 0.1 to 5 mg/kg, 0.1 to 4 mg/kg, or 0.1 to 3 mg/kg body weight.

The molar ratio of the polypeptide to the inner leaflet component in an agent of the present disclosure is in the range from about 1:1 to about 1:50, preferably about 1:1 to about 1:25, more preferably about 1:1 to about 1:10, yet more preferably about 1:7 or about 1:3. Suitable ratios include, but are not limited to, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:30, 1:35, 1:40, 1:45, and 1:50. The mass ratio of the polypeptide to the inner leaflet component in an agent of the present disclosure is in the range from about 15:1 to about 3:10, preferably about 15:1 to about 3:5, more preferably about 15:2 to about 3:0, yet more preferably about 15:7 or about 5:1. It is recognized that the preferred ratio of the polypeptide and inner leaflet component in an agent of the invention may be affected by certain factors such as, but not limited to, the target cell type.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with a therapeutically effective amount of the agent one time per week for between about 1 to 10 weeks, preferably between about 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

Where a subject undergoing therapy exhibits a partial response or a relapse following a prolonged period of remission, subsequent course of treatment with an agent of the invention may be administered. Thus, subsequent to a period of time off from a first treatment period, which may have comprised a single dosing regimen or a multiple dosing regimen, a subject may receive one or more additional treatment periods comprising single or multiple dosing regimens. Such a period of time off between treatment periods is referred to herein as a time period of discontinuance. It recognized that the length of the time period of discontinuance is dependent upon the degree of tumor response achieved with any prior treatment periods with the anti-tumor agents of the present disclosure.

The pharmaceutical compositions can be included in a container, pack, or dispenser together with instructions for administration.

The results of treatment of a cancer may be assayed by any method known to one skilled in the art including, but not limited to, physical examination, laboratory, nuclear, and radiographic studies (i.e., computer tomography and/or magnetic resonance imagery), ultrasound, or other procedures.

Further provided herein are kits for the preparation of a pharmaceutical composition or for treating a cancer. Many embodiments of such kits are possible. For instance, a kit could house three containers, the first container comprising a saposin C-related polypeptide and a phospholipid, the second container comprising a mTOR inhibitor, and the third container comprising a pharmaceutically acceptable diluent, carrier, or excipient. In certain embodiments, the saposin C-related polypeptide has an amino acid sequence at least 75% identical to the entire length of SEQ ID NO: 2. In certain embodiments, the mTor inhibitor comprises a rapamycin compound. The kits typically further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

The principle and mode of operation of this invention have been explained and illustrated in its preferred embodiment. However, it must be understood that this invention may be practiced otherwise than as specifically explained and illustrated without departing from its spirit or scope.

EXAMPLES

Example 1

Synergy analysis was completed using CompuSyn software. Western blot, fluorescent microscopy, FACS analysis, MTT viability assays, and transmission electron microscopy were used to check for molecular markers.

SapC-DOPS treatment of neuroblastoma cells induced caspase dependent apoptosis. Interestingly, western blot analysis of primary glioma neurospheres treated with SapC-DOPS did not show any activation of apoptosis through cleaved caspase 9 or cleaved PARP, and lacked activation of DNA damage markers P-ATM and y-H2AX, and ER stress through BiP and IRE1α. Pretreatment with the pan-caspase inhibitor Z-VAD-FMK did not rescue SapC-DOPS-induced killing, indicating it was caspase independent ($P>0.05$).

To investigate the possible influence of p53, the inventors utilized a GBM cell line expressing tet inducible p53. SapC-DOPS-induced killing was unaffected by the presence of p53 in these cells. Treatment with SapC-DOPS also yielded no cell cycle arrest as determined by PI incorporation and FACS analysis. Alternatively, treatment of primary glioma neurospheres as well as serum-based cells resulted in increased levels of the autophagic marker LC3-II via western blot. Autophagosome formation was also confirmed through transmission electron microscopy (TEM).

Figure 3:
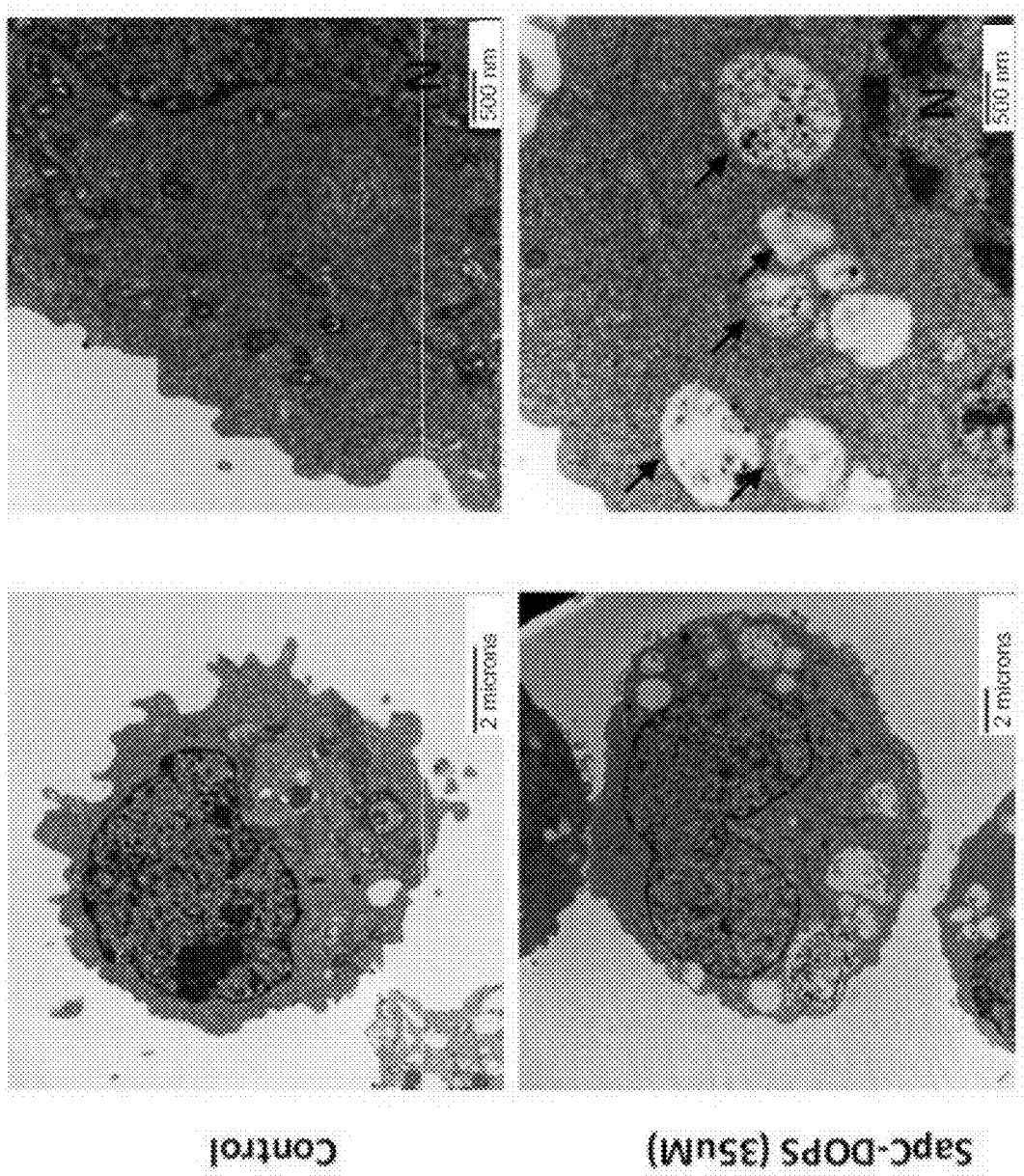
FIG. 3: SapC-DOPS induces autophagosome formation.

Utilizing a stable glioma cell line expressing a GFP-LC3 fusion protein, the inventors observed punctuated GFP expression following treatment, which is indicative of autophagosome formation. Quantification of GFP punctuated cells showed a significant increase in SapC-DOPS treated cells compared to control ($P<0.001$). (FIG. 3.) Analysis of red/green fluorescence following acridine orange staining showed an induction of acidic vesicular organelles, indicative of autophagolysosomes.

Further, inhibition of autophagosome formation using 3-methyladeneine or inhibition of autophagic vacuole maturation with bafilomycin A1 resulted in a significant rescue of SapC-DOPS-induced killing ($P<0.001$). Knockdown of ATG5 using siRNA also resulted in a rescue of SapC-DOPS-induced cell death and autophagy induction ($P<0.001$). While beclin-1 (inducer of autophagy) levels remained constant following treatment, the inventors did observe a significant reduction in the levels of Bcl-2, which is a known inhibitor of beclin-1 induced autophagy.

Figure 4:
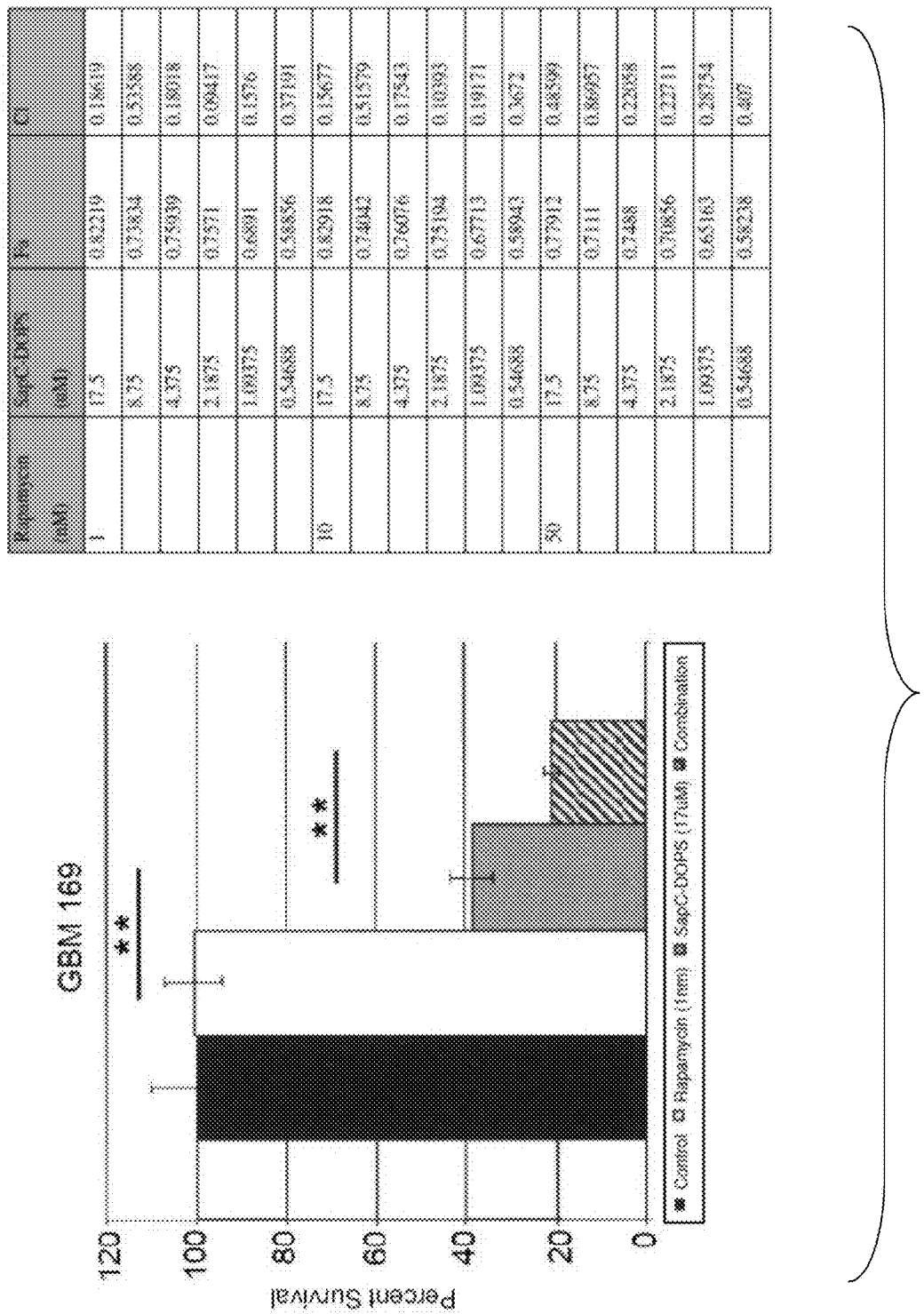
FIG. 4: Inhibition of mTOR with rapamycin in combination with SapC-DOPS results in strong synergy.
Figure 5:
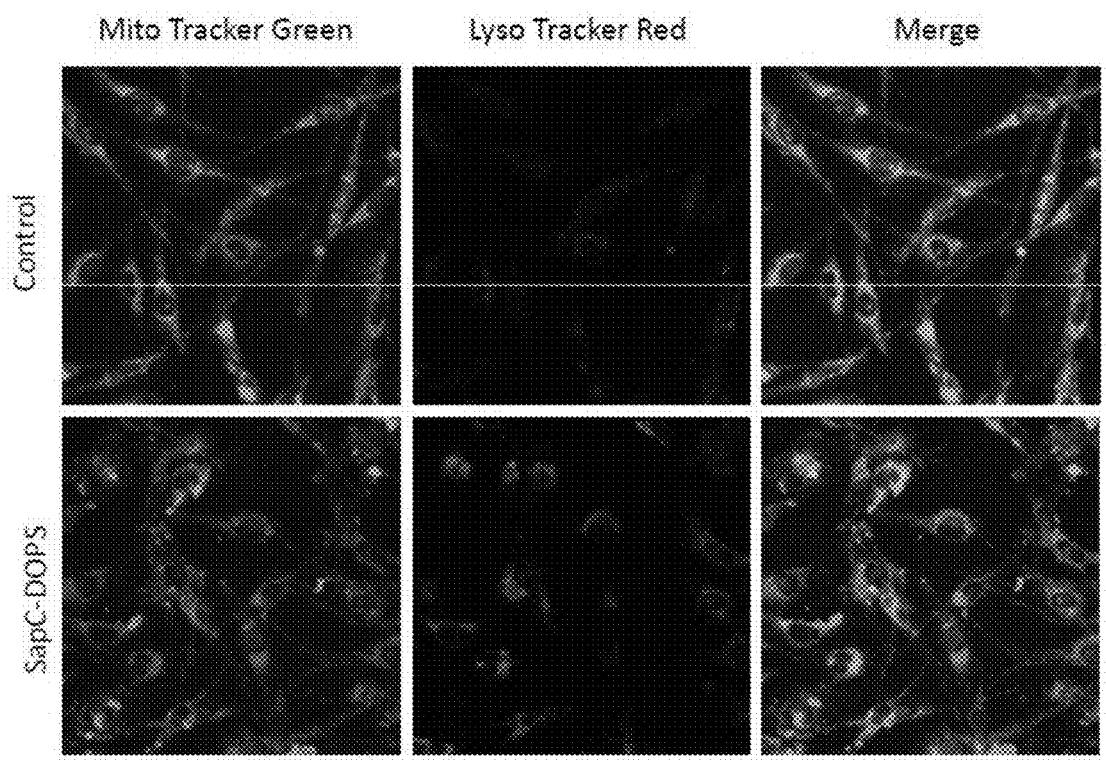
FIG. 5: SapC-DOPS induces mitophagy.

Rapamycin was tested in combination with SapC-DOPS. Using the Chou Talay analysis for synergy, the inventors were able to show strong synergy for multiple drug combinations in primary glioma neurospheres (combination index<0.4). (FIG. 4.) To investigate whether SapC-DOPS induced autophagy could be preferentially targeting mitochondria (mitophagy), MitoTracker Green (mitochondria) and LysoTracker Red (autophagolysosomes) were utilized. Using confocal microscopy analysis, a decrease in mitochondria in cells treated with SapC-DOPS, as well as co-localization between mitochondria and autophagolysosomes, was observed. (FIG. 5.)

These findings show that lethal mitophagy is a mechanism for SapC-DOPS-induced cell death in GBM. Moreover, the present disclosure provides glioblastoma treatments comprising synergistic combinations of P13K inhibitor(s) with mTOR inhibitor(s), including combination P13K/mTOR dual inhibitor(s).

Example 2

The systemic use of SapC-DOPS was evaluated in several models of brain cancer, including glioblastoma multiforme (GBM).

To evaluate if SapC-DOPS could effectively target glioma cells in vitro, SapC-DOPS nanovesicles labeled with the lipophilic fluorescent probe CellVue Maroon (CVM) were utilized. Initial targeting was tested using U87ΔEGFR cells, human glioma cells harboring EGFRvIII: a truncated, constitutively active, mutant epidermal growth factor receptor (ΔEGFR). EGFR amplification is the most common genetic alteration in GBM and many of the tumors overexpressing EGFR also harbor the constitutively active form EGFRvIII, a strong prognostic indicator of poor survival.

Figure 6A:
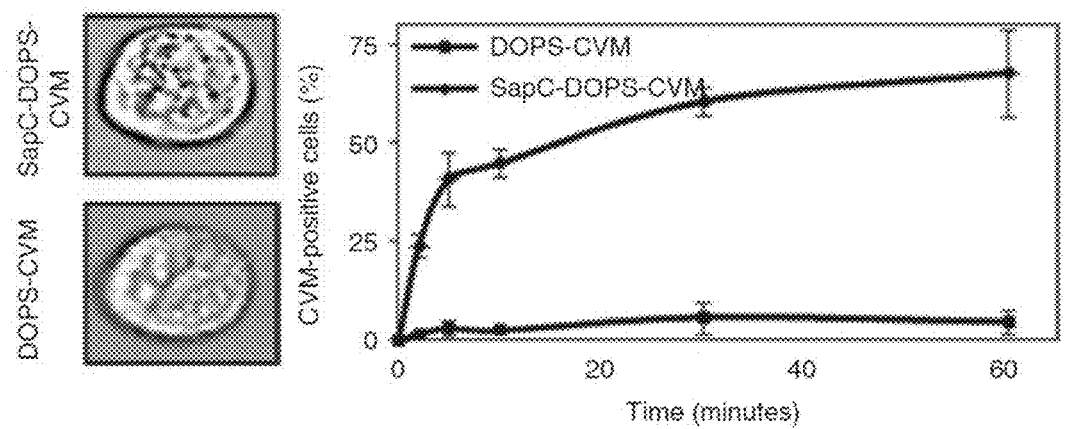
FIGS. 6A-D: SapC-DOPS efficiently targets glioblastoma multiforme (GBM) cells in vitro and in vivo. (A) Fluorescent microscopy images of U87ΔEGFR-Luc cells treated with CellVue Maroon (CVM)-labeled SapC-DOPS (top) and control CVM-labeled DOPS (bottom panel) showing ability of SapC-DOPS to target GBM cells in vitro. Right panel is quantification of targeting by imaging flow cytometry ±SD. (B) Fluorescence images of brains (superimposed by bright field) of mice bearing intracranial glioma (X12v2 cells) treated with intravenous SapC-DOPS-CVM (top) or DOPS-CVM 10 days post-tumor cell implantation. (C, D) Fluorescent IVIS images of spontaneous tumor bearing (C) Mut6 and (D) cKO mice treated with a single dose of SapC-DOPS-CVM. Hematoxylin and eosin (H&E) staining of tumor-bearing brain sections imaged in (D). CPC, choroid plexus carcinoma; GFP, green fluorescent protein; SapC-DOPS, Saposin C-dioleoylphosphatidylersine.
Figure 6B:
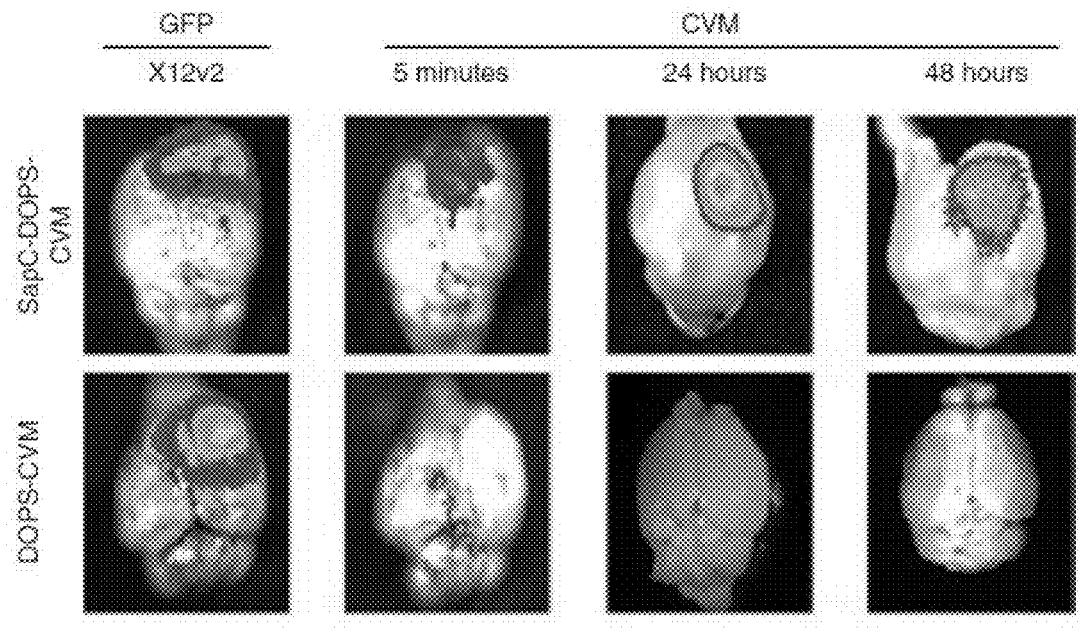

Following treatment of U87ΔEGFR-Luc cells with SapC-DOPS-CVM, accumulation of CVM within the cell membrane was evident by fluorescent microscopy. Quantification of the targeting by flow cytometry revealed that SapC-DOPS was incorporated into glioma cell membranes within minutes and remained stably incorporated in the cell membrane for up to an hour (FIG. 6A). To determine if SapC-DOPS could target human GBM cells in vivo, green fluorescent protein-expressing primary GBM-derived X12v2 cells (FIG. 6B) or U87ΔEGFR-Luc cells were implanted intracranially into mice. Ten days following tumor cell implantation, mice were treated intravenously with SapC-DOPS-CVM by tail vein injection and its localization was evaluated by monitoring fluorescence by the IVIS 200 imaging system (FIG. 6B). Consistent with the rapid targeting observed in vitro, SapC-DOPS-CVM was found to localize to intracranial tumors within minutes of intravenous injection, and persisted for up to 48 hours post-treatment. Fluorescent microscopy of frozen sections of tumor-bearing brains from these mice revealed that SapC-DOPS-CVM co-localized with green fluorescent protein-expressing GBM cells in vivo. No fluorescence signal was detected in normal non-neoplastic brain parenchyma.

Figure 6C:
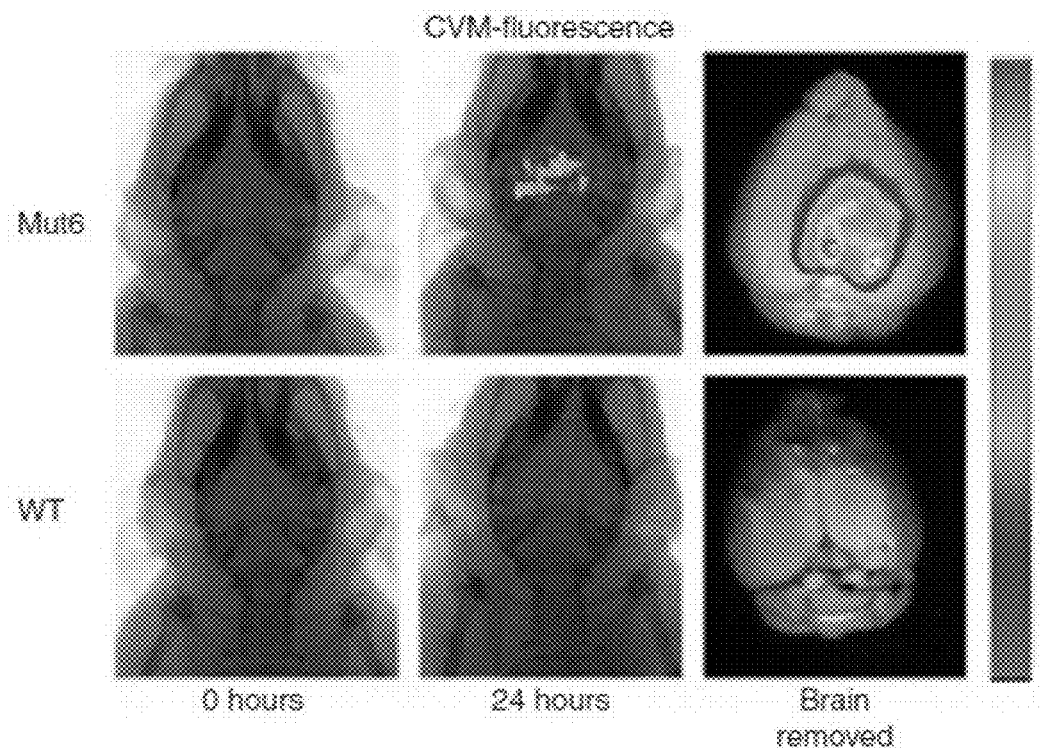
Figure 6D:
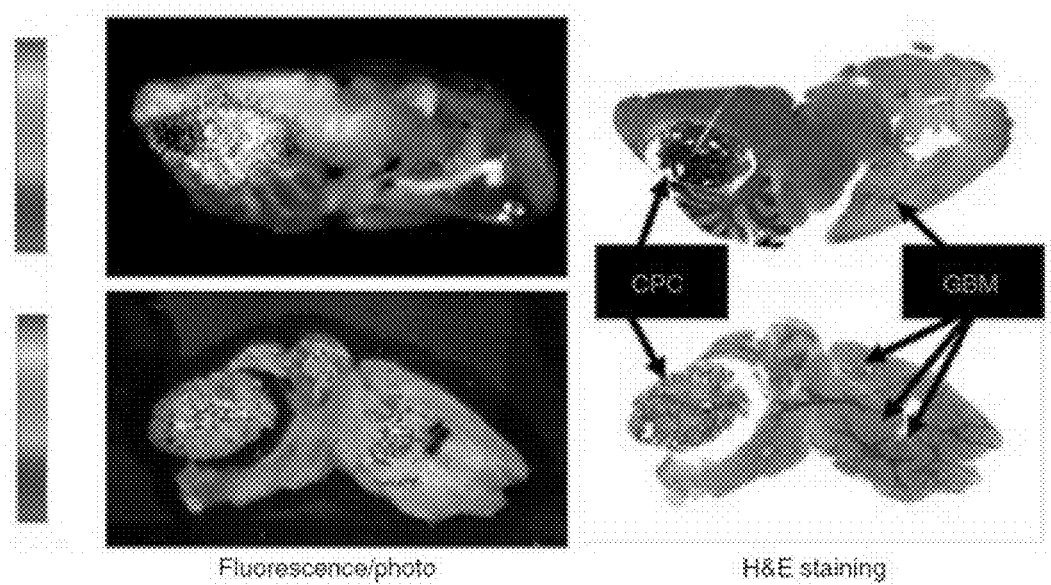

To further confirm the ability of SapC-DOPS to cross the BBTB, two genetically engineered mouse models which develop spontaneous brain tumors were utilized. Mut6 mice (FGAP-cre; Nf1$^{loxP/+}$; p53$^{-/loxP}$; Pten$^{loxP/+}$) and quadruple cKO mice (GFAP-CreER; Pten$^{loxP/loxP}$; p53$^{loxP/loxP}$; Rb1$^{loxP/loxP}$; p107$^{-/-}$) were obtained and monitored daily for development of neurological symptoms (seizures, paralysis, etc.). Once symptoms of tumor burden (mild hemiparesis, lack of grooming, or lethargy) were observed (~15 weeks for Mut6 and 10 weeks for quadruple cKO), mice were treated with a single intravenous dose of SapC-DOPS-CVM and imaged 24 hours later. Tumor-specific CVM fluorescence was observed in both Mut6 and quadruple cKO spontaneous glioma-bearing mice (FIGS. 6C, 6D). cKO mice occasionally develop choroid plexus carcinoma, a rare brain tumor which occurs mainly in young children. Histological analysis of the brains from these mice revealed efficient targeting of choroid plexus carcinoma as well as small foci of spontaneous glioma by SapC-DOPS-CVM (FIG. 6D). These data demonstrate that SapC-DOPS can effectively cross the BBTB to selectively target brain tumors in vivo.

Figure 7A:
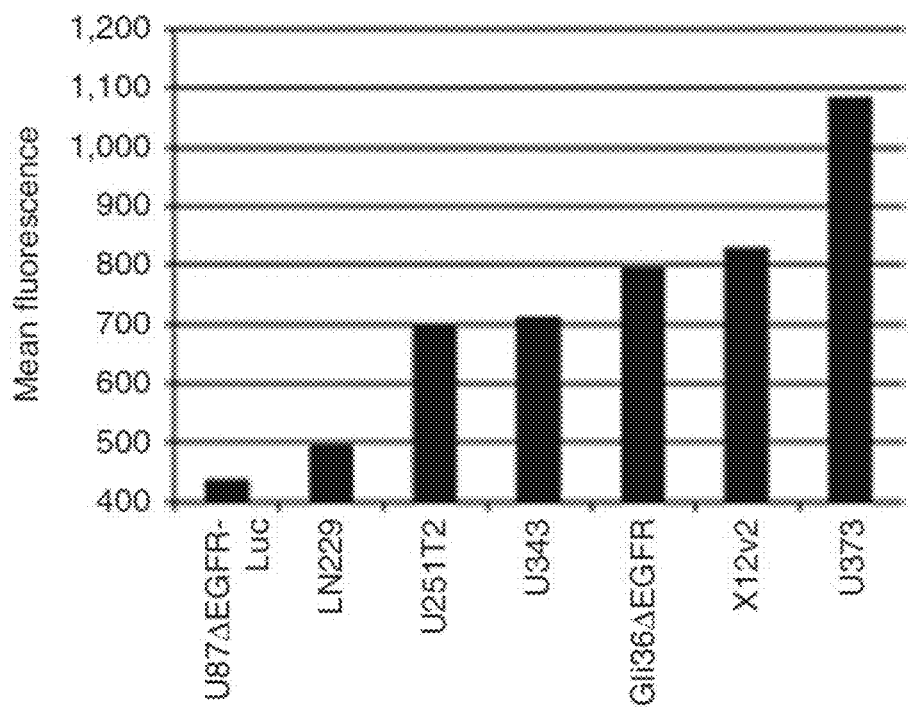
FIGS. 7A-C: SapC-DOPS targets exposed phosphatidylserine on glioma cells in vitro and in vivo. (A) Quantification of the mean fluorescence of exposed PtdSer in a panel of glioblastoma multiforme (GBM) cell lines. (B) Percent survival of GBM cells 72 hours after treatment with SapC-DOPS (SapC 50 mol/l). Data shown are mean values of percent surviving cells for low and high PtdSer-expressing cell lines. **P=0.01. (C) Representative luminescent and fluorescence IVIS images of mice implanted subcutaneously with U87ΔEGFR-Luc cells incubated with lactadherin (Lact-C2), β-2-glycoprotein-1 (β2GP1), or PBS, after intravenous treatment with SapC-DOPS-CVM, respectively. CVM, CellVue Maroon; SapC-DOPS, Saposin C-dioleoylphosphatidylserine; PBS, phosphate-buffered saline; PtdSer, phosphatidylserine.
Figure 7B:
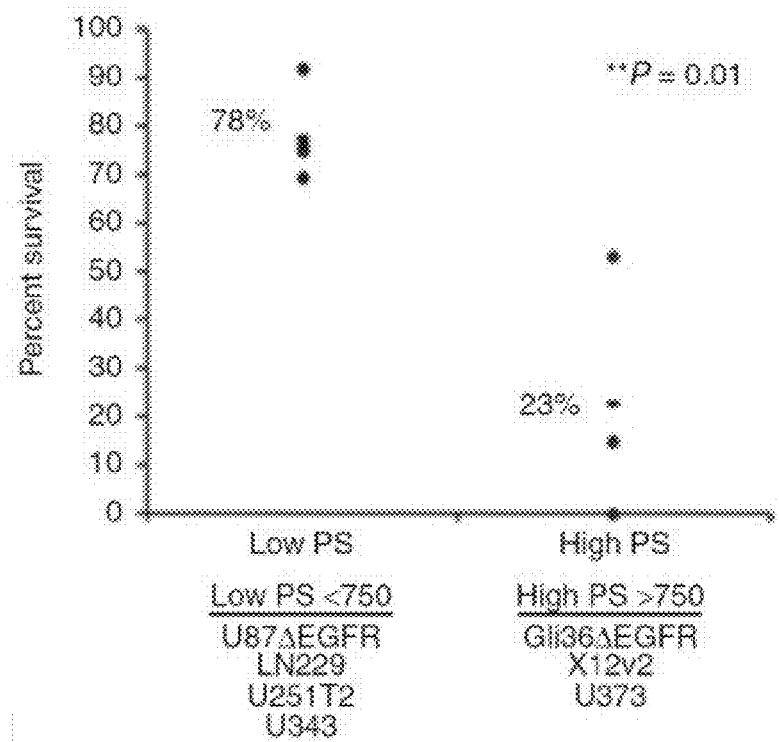

Collectively, the data displayed a very high specificity of SapC-DOPS for neoplastic brain tumor cells with minimal effects on non-neoplastic normal brain. The specificity of SapC-DOPS for glioma was further evaluated by analyzing its targeting mechanism. SapC is known to associate and fuse to negatively charged phospholipids including PtdSer. Normally sequestered on the inner leaflet of the cell membrane, PtdSer is externalized to the outer leaflet of plasma membrane of neoplastic cells. To evaluate if cancer cell specificity of SapC-DOPS is dependent on surface exposure of PtdSer, sensitivity of GBM cells was compared with low or high surface exposure of PtdSer to SapC-DOPS-induced cytotoxicity. GBM cells expressing high surface levels of PtdSer were significantly more sensitive to SapC-DOPS treatment compared with GBM cells with low PtdSer exposure levels (FIGS. 7A, 7B).

Figure 7C:
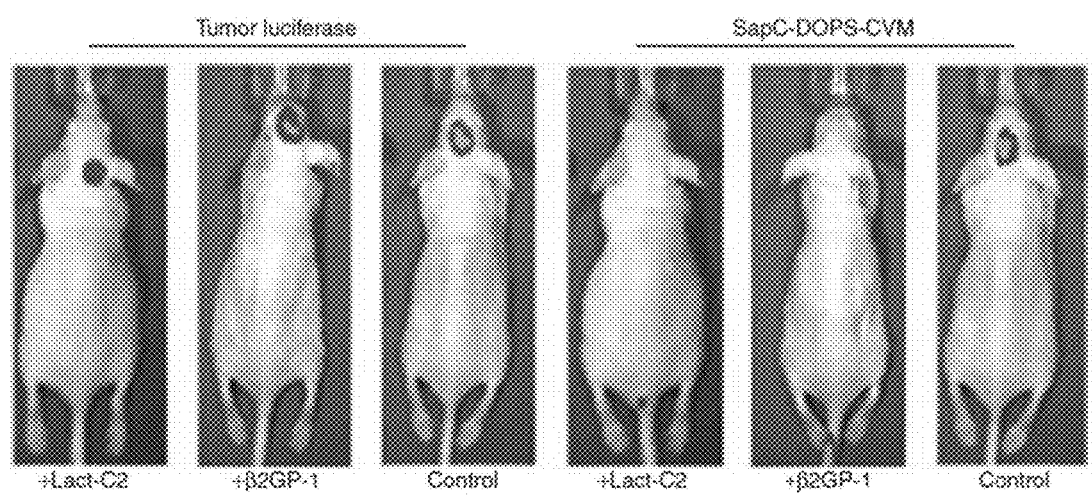

To further corroborate this discovery in vivo, the ability of the PtdSer-specific binding proteins lactadherin C2 (Lact-C2) and β-2-glycoprotein-1 (β2GP1) to block in vivo targeting of SapC-DOPS to GBM was evaluated. U87ΔEGFR-Luc cells were incubated with Lact-C2 or β2GP1 before subcutaneous implantation into nude mice. Cells were implanted under the skin and not intracranially to permit visualization of signal without allowing cells to proliferate and lose cell surface bound Lact-C2 or β2GP1 proteins (FIG. 7C). Because many tumors contain high levels of dead and dying cells which expose PtdSer, whether SapC-DOPS preferentially targets areas of necrosis containing high levels of dead or dying cells was evaluated. To do this, subcutaneous U87ΔEGFR-Luc tumors were established in mice an allowed to grow to a large size of 1,500 mm$^3$ (a size in which large areas of necrosis are known to exist). Then, the mice were treated with a single dose of SapC-DOPS-CVM. Tumors were harvested 24 hours later for immunofluorescence. Fluorescent imaging of CVM shows SapC-DOPS localization in both necrotic and non-necrotic tumor tissue. Collectively, these results indicate that PtdSer exposure on GBM cells is important for SapC-DOPS targeting in vivo.

Figure 8A:
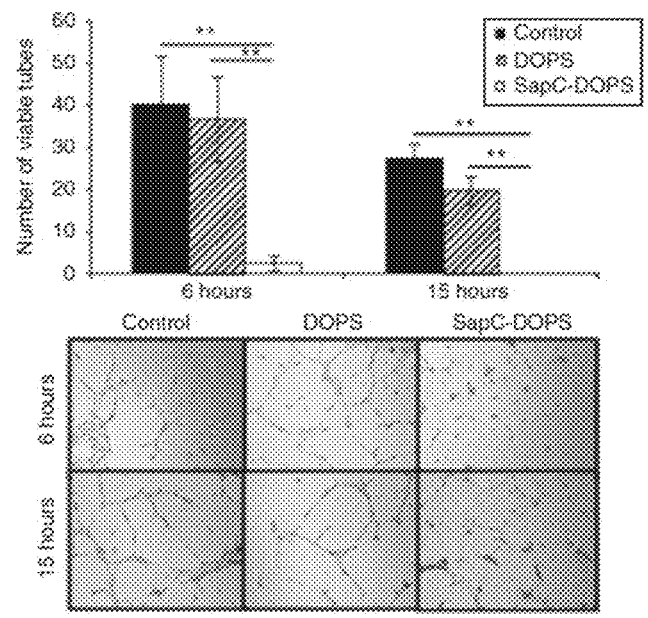
FIGS. 8A-F: Antiangiogenic effects of SapC-DOPS in vitro and in vivo. (A) Inhibition of endothelial cell tube formation by SapC-DOPS. Human dermal microvascular endothelial cells (HDMECs) were incubated with SapC-DOPS, DOPS, or control (media alone). Cells were then plated onto polymerized Matrigel. Six and 15 hours post-plating, the number of tubes-view field were quantified. Data shown are mean number of tubes/view field ±SD, P<0.01. Bottom panel shows representative images of endothelial cell tubes from each group. (B) Reduced migration of HDMECs treated with SapC-DOPS. HDMECs treated with SapC-DOPS, DOPS, or control (media alone) were allowed to migrate in a standard Boyden chamber assay, and the number of cells that migrated to the other side of the membrane was quantified. Data shown are mean number of cells/view field ±SD. Representative fluorescent images of migrated cells stained with Hoecst, P<0.001. (C) Reduced ex vivo sprouting of rat aorta rings treated with SapC-DOPS. One millimeter thick rings of rat aorta rings treated as indicated were plated in Matrigel, and the amount of endothelial sprouting was analyzed 48 hours later. Shown are representative images of sprouting aorta from n=4/group. (D) SapC-DOPS targets tumor vasculature in vivo. Immunofluorescent images (20×) from the brains of mice bearing intracranial U87ΔEGFR tumors treated with SapC-DOPS: His-tag (green), CD31 (red), and DAPI (blue). (E) Immunofluorescent images from brains in (D) stained with CD31 (red), cleaved caspase-3 (green), and DAPI (blue). Dotted white line divides tumor (left) from normal brain parenchyma (right). (F) SapC-DOPS reduced angiogenesis in vivo. Subcutaneous Gli36ΔEGFR tumor bearing mice (100-200 mm$^3$) were treated with five consecutive daily doses of SapC-DOPS or DOPS control, and then analyzed for microvessel density as described. Data shown are mean MVD ±SD for each group, n=2-4 sections/tumor and n=4 tumors/group, **P=0.001. Bottom shows representative images of tumor sections analyzed by immunohistochemistry for CD31 to highlight blood vessels. Bars=100 μmol/l. DAPI, 4',6-diamidino-2-phenylindole; MVD, microvessel density; SapC-DOPS, Saposin C-dioleoylphosphatidylserine.
Figure 8B:
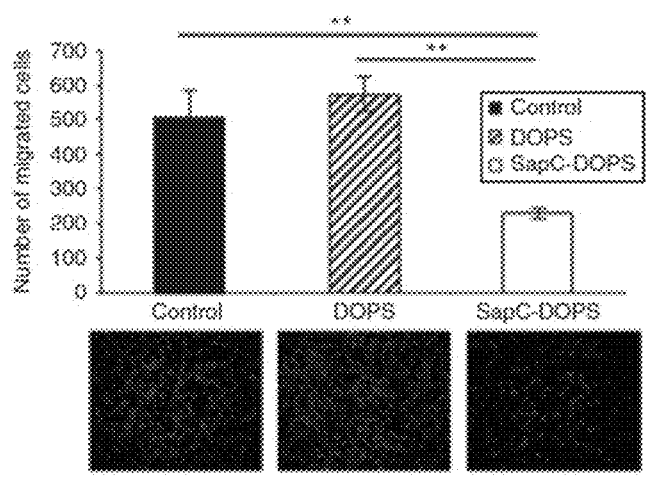
Figure 8C:
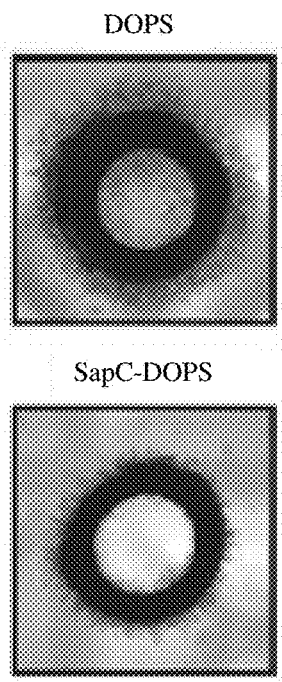

In light of the specificity of SapC-DOPS for PtdSer, the impact of SapC-DOPS on angiogenesis in brain tumors was evaluated. First it was determined that proliferating endothelial cells succumbed to SapC-DOPS-induced cytotoxicity at comparable doses to GBM cells in vitro. Treatment of human dermal microvascular endothelial cells (HDMECs) (FIG. 8B) and human umbilical vein endothelial cells (HUVECs) with SapC-DOPS caused a significant inhibition of cell migration in a standard Boyden chamber assay, and nearly abolished the viable tube formations of HDMECs (FIG. 8A) and HUVECs on Matrigel. SapC-DOPS also substantially inhibited vessel sprouting in the ex vivo rat aortic ring assay (FIG. 8C).

Figure 8D:
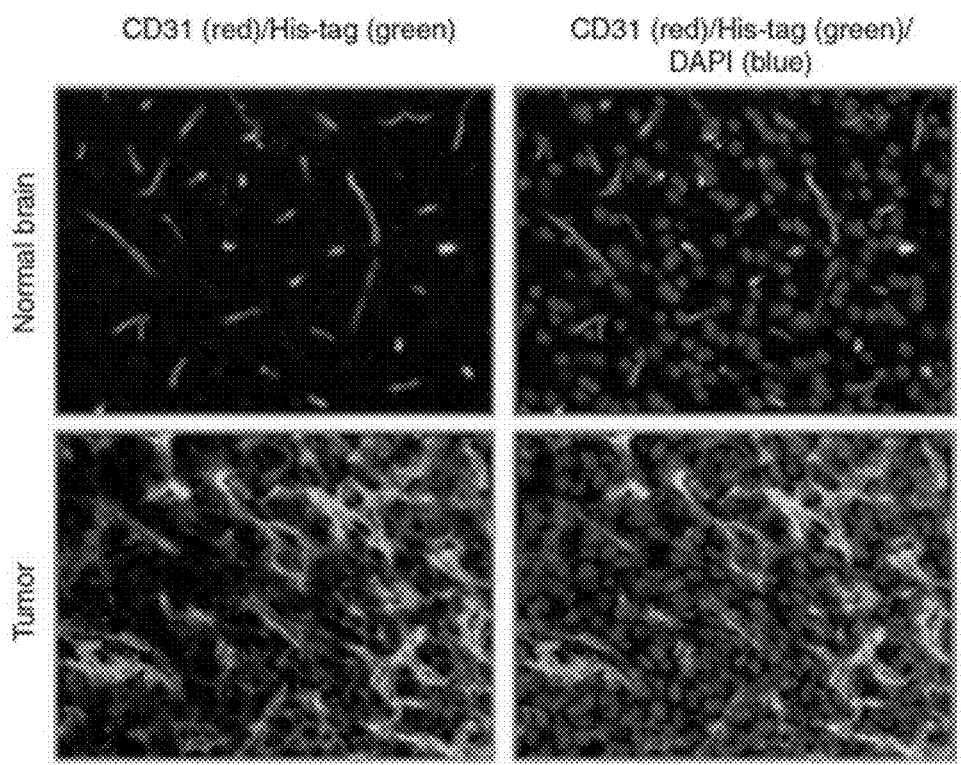
Figure 8E:
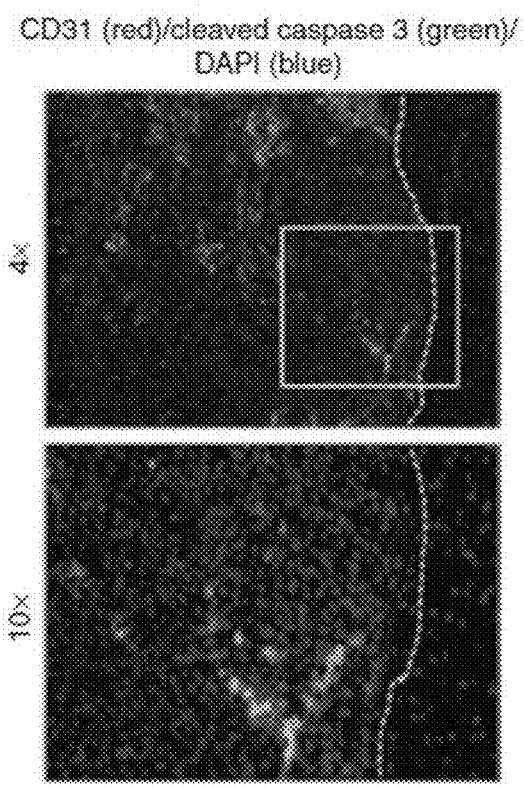

To evaluate whether SapC-DOPS targets the tumor vasculature in vivo, U87ΔEGFR glioma cells were implanted intracranially in nude mice. Mice were treated 11 days later with a single dose of His-tagged SapC-DOPS or DOPS control Animals were then killed and their brains were harvested for immunofluorescence analysis 3 hours later. Co-localization of SapC-DOPS (His-tag) with the tumor vasculature (CD31) and glioma cells (DAPI (4',6-diamidino-2-phenylindole)) was observed within the tumor (FIG. 8D). His-tag staining was found to be absent in the normal brain parenchyma, including both the normal blood vessels and normal neuronal cells. Furthermore, co-localization (yellow) of CD31 (red) and cleaved caspase-3 (green) was observed within the tumor but not in the normal brain (FIG. 8E). These results attest to the specificity of SapC-DOPS targeting of glioma cells and the tumor vasculature as opposed to normal brain tissue.

Figure 8F:
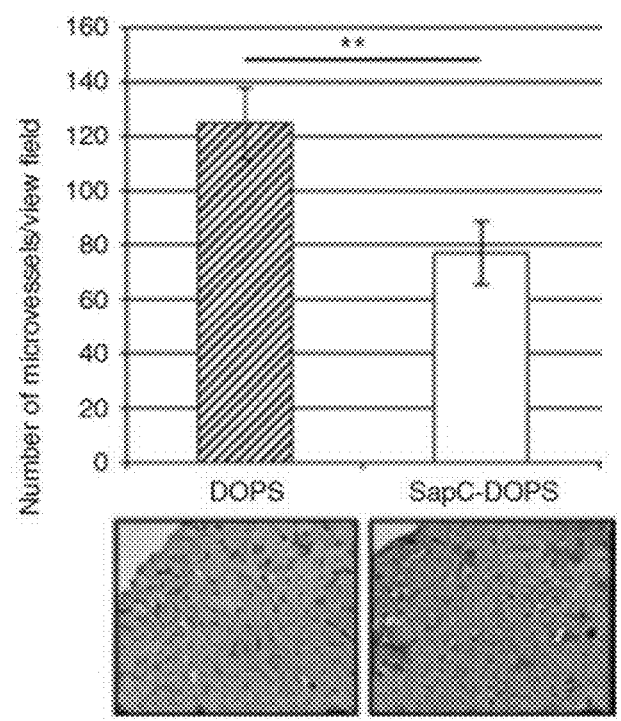

To elucidate the effect of SapC-DOPS on the tumor vasculature in vivo, nude mice with established subcutaneous GBMs (100-200 mm$^3$) were treated with five consecutive daily doses of SapC-DOPS or DOPS control. Twenty-four hours following the final treatment, animals were killed and the tumors were harvested for immunohistochemistry analysis. Quantification of CD31-positive microvessels demonstrated a remarkable reduction in the microvessel density of GBMs treated with SapC-DOPS compared with DOPS control (FIG. 8F). Overall, these results reveal strong antiangiogenic effects of SapC-DOPS.

Figure 9A:
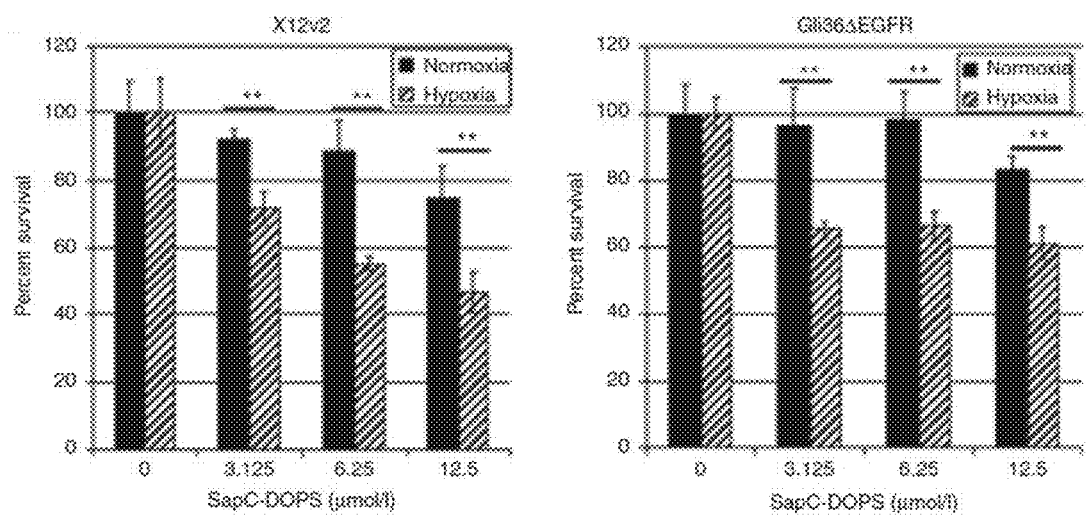
FIGS. 9A-B: Glioblastoma multiforme (GBM) cells show higher sensitivity to SapC-DOPS and increased levels of PtdSer in hypoxia. (A) X12v2 or Gli36ΔEGFR cells were treated with the indicated doses of SapC-DOPS in normoxia (20% $O_2$) or hypoxia (1% $O_2$) for 72 hours and cell viability was measured by MTT. All values were normalized to untreated control cells in normoxia or hypoxia. Data shown are mean±SD of percentage viable cells after treatment with SapC-DOPS in normoxia or hypoxia, **P<0.01. (B) PtdSer exposure was measured by flow cytometry using Annexin V-Pacific Blue following 72 hours of normoxia or hypoxia. MTT, 3-(4,5-dimethylthiazol-2-yl)-2,5-diphenyltetrazolium bromide; PtdSer, phosphatidylserine; SapC-DOPS, Saposin C-dioleoylphosphatidylserine.
Figure 9B:
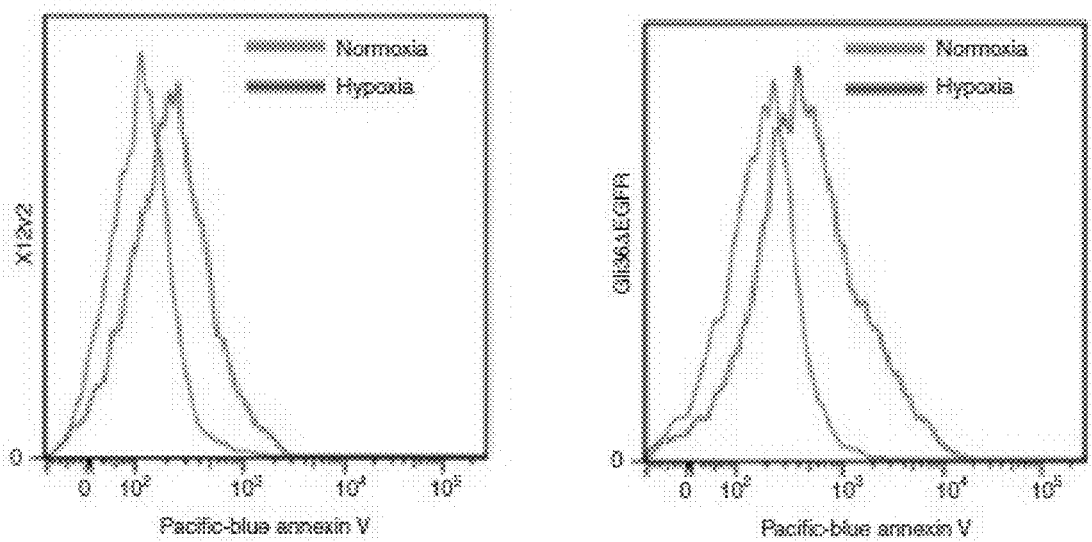

Antiangiogenic therapy for high grade GBM has been associated with tumor vessel destruction resulting in elevated tumoral hypoxia. Tumoral hypoxia is recognized for its influence in resistance to standard therapeutics, including ionization radiation and chemotherapy. Since SapC-DOPS possesses significant antiangiogenic effects, as shown above, the efficacy of SapC-DOPS in a hypoxic environment was evaluated. Cell viability of Gli36ΔEGFR and X12v2 cells treated with effective SapC-DOPS doses in hypoxia (1% $O_2$) or normoxia (20% $O_2$) revealed increased sensitivity to SapC-DOPS-induced cytotoxicity in hypoxia (FIG. 9A). The impact of hypoxia on cell surface PtdSer exposure was also evaluated. Fluorescence-activated cell sorting analysis of GBM cells following 72 hours incubation in hypoxia compared with normoxia revealed a significant increase in exposed PtdSer on the outer membrane (FIG. 9B).

Figure 10A:
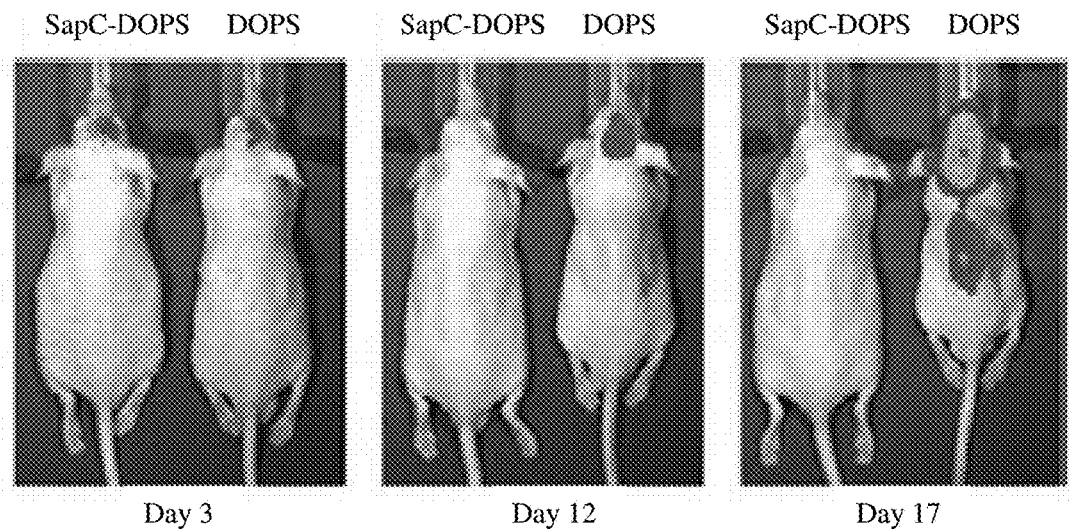
FIGS. 10A-C: Intravenous administration of SapC-DOPS yields significant antitumor efficacy in vivo. (A) U87ΔEGFR-Luc cells were implanted intracranially and treated with SapC-DOPS. Images were taken for tumor luminescence at 3, 2, and 17 days post-tumor implantation. (B, C) Kaplan-Meier survival curve for mice with intracranial (B) U87ΔEGFR-Luc and (C) X12v2 glioma treated with intravenous injections of DOPS or SapC-DOPS. SapC-DOPS, Saposin C-dioleoylphosphatidylserine.
Figure 10B:
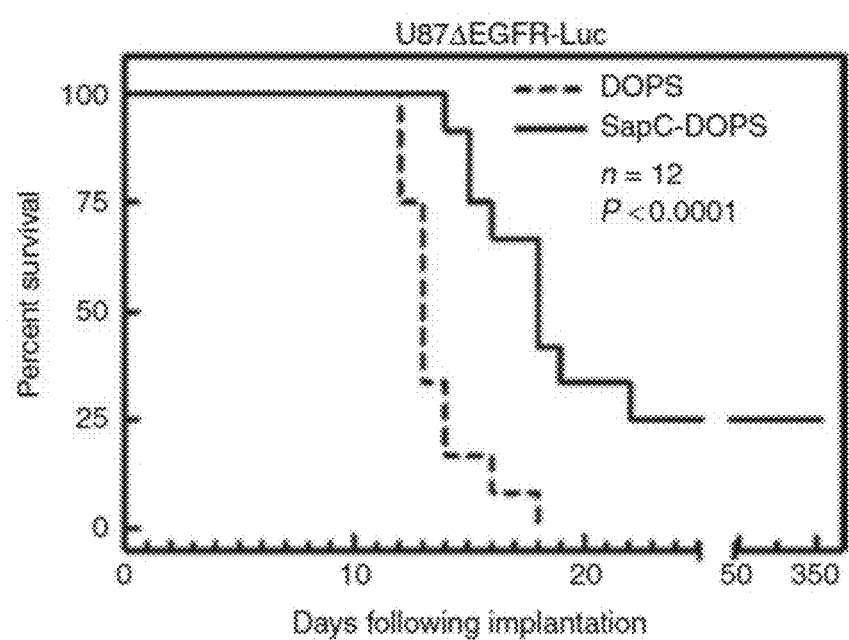
Figure 10C:
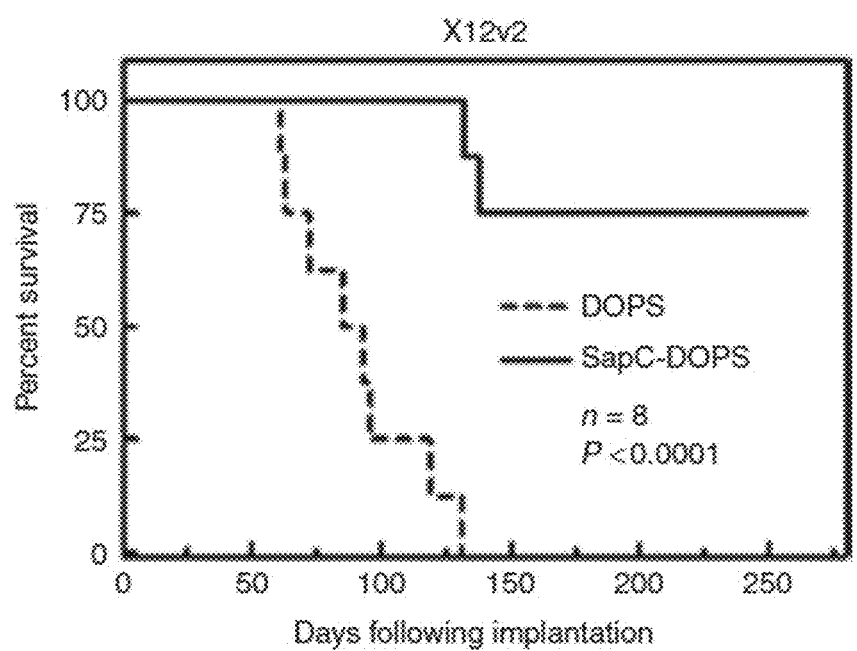

The in vivo antitumor efficacy of SapC-DOPS in mice bearing intracranial tumors was assessed. Mice with intracranial U87ΔEGFR-Luc tumors were treated with SapC-DOPS or control DOPS intravenously, and tumor progression was followed by in vivo imaging of tumor cell expressed luminescence as indicated (FIG. 10A). Tumor burden could be visualized by luminescence imaging as early as 3 days post-implantation, and while control DOPS-treated animals showed progressive tumor growth until day 17, no detectable tumor could be found in mice treated with SapC-DOPS (FIG. 10A). To elucidate the antitumor efficacy of SapC-DOPS, survival of the mice with intracranial tumors was compared in two different tumor models: U87ΔEGFR-Luc and X12v2 with low and high PtdSer exposure, respectively (FIGS. 10B, 10C). While SapC-DOPS treatment resulted in a significant increase in survival in both models, only 25% of the mice implanted with PtdSer low U87ΔEGFR-Luc tumors were long-time survivors, whereas 75% of the mice implanted with high PtdSer-expressing X12v2 tumors were long-term survivors. Systemic treatment with SapC-DOPS is thus able to target GBM tumors with both low and high levels of exposed PtdSer in vivo, yielding a significant increase in survival in both models.

This example demonstrates the ability of SapC-DOPS to selectively and effectively cross the blood-brain tumor barrier (BBTB) to target brain tumors in vivo, and further reveals the targeting to be contingent on the exposure of the anionic phospholipid phosphatidylserine (PtdSer). Increased cell surface expression of PtdSer levels was found to correlate with SapC-DOPS-induced killing efficacy, and tumor targeting in vivo was inhibited by blocking PtdSer exposed on cells. Apart from cancer cell killing, SapC-DOPS also exerted a strong antiangiogenic activity in vitro and in vivo. Unlike traditional chemotherapy, hypoxic cells were sensitized to SapC-DOPS-mediated killing.

In this example, human GBM cell lines were obtained from ATCC (Manassas, Va.), Gli36 cells subcloned to express a truncated, constitutively active, mutant epidermal growth factor receptor (Gli36ΔEGFR), UB87ΔEGFR, and UB87ΔEGFR-Luc, were obtained from the Ludwig Cancer Institute (San Diego, Calif.), X12 primary tumor-derived cells were obtained from the Mayo Clinic (Rochester, Minn.) and were subcloned to express green fluorescent protein to generate X12v2. All cells were routinely checked for *mycoplasma* contamination. Cells were cultured with Dulbecco's modified Eagle's medium supplemented with 10% fetal bovine serum, 100 units of penicillin/ml, and 10 mg of streptomycin/ml. HDMECs and HUVECs were purchased from ScienCell Research Laboratories (San Diego, Calif.) and cultured with endothelial cell medium supplemented with 2% fetal bovine serum, 100 units of penicillin/ml, and 10 mg of streptomycin/ml. All cells were cultured at 37° C. in an atmosphere containing 5% $CO_2$ and 20% $O_2$ for normoxia and 1% $O_2$ for hypoxia. For cytotoxicity assays, cells were plated at 10,000 cells/well in 96-well dishes overnight and treated with SapC-DOPS for 72 hours. Cell viability was determined as described using a standard MTT (3-(4,5-dimethylthiazol-2-yl)-2,5-diphenyltetrazolium bromide) assay. PtdSer-specific binding proteins, Lact-C2 and β2GP1 were obtained from the Department of Veterans Affairs, VA Boston Healthcare System, Brigham and Women's Hospital, Harvard Medical School (Boston, Mass.) and Haematologic Technologies (Essex Junction, Vt.). Exposed PtdSer on cells was measured using binding of Annexin V-Pacific Blue purchased from Invitrogen (Carlsbad, Calif.) and was used according to the manufacturer's instructions.

To prepare the SapC and SapC-DOPS nanovesicles, recombinant SapC with and without His-tag were expressed using the pET system in *Escherichia coli* cells. Expressed SapC was purified by ethanol precipitation and ion-exchange high-performance liquid chromatography. After lyophilization using a tertiary butyl alcohol/water co-solvent system, protein powder was used and its concentration was determined by its weight. All phospholipids were purchased from Avanti Polar Lipids (Alabaster, Ala.). SapC-DOPS nanovesicles were prepared by two methods: (1) Bath sonication after solvent removal under nitrogen gas, and (2) lyophilization with a co-solvent solution. For the bath sonication, DOPS was mixed with weighed dry amounts of SapC in an acid buffer (pH 5) and quickly diluted in phosphate-buffered saline or media. The mixture was then sonicated to assemble into nanovesicles. The sonicated samples were stored at 4° C. For lyophilization, dry DOPS was suspended in 80% tert-butanol. SapC and sucrose (10 mg/ml) were dissolved in water. The mixture of DOPS and SapC plus sucrose (1:0.6, vol:vol) was lyophilized to a stable powder cake in a freeze dryer (VirTis Unitop 1000L linked to a Freezemobile 25XL). The cake was resuspended in phosphate-buffered saline or media to form SapC-DOPS nanovesicles. Once formed, the vesicles were monitored by a N4 plus subsize particle size analyzer. SapC-DOPS for in vitro experiments was formulated at a 1:3 molar ratio of SapC:DOPs.

For the intracranial tumor evaluations, anesthetized mice were fixed in a stereotactic apparatus, and U87ΔEGFR-Luc ($1 \times 10^5$ cells) or X12v2 (green fluorescent protein) ($2 \times 10^5$ cells) were implanted at 2 mm lateral to bregma, at a depth of 3 mm. For survival evaluations, mice were treated with SapC-DOPS (SapC 12 mg/kg, DOPS 4.6 mg/kg) or DOPS (4.6 mg/kg) intravenously on the following days post-tumor implantation: 4-11, 13, 15, 17, 19, 22, 25, 28, and 31 days for U87ΔEGFR-Luc tumors and 5-9, 11, 13, and 15 days for X12v2 tumors. For tests involving CD31 and cleaved caspase-3 staining, mice were treated on days 6-10 following implantation, and brains were harvested 24 hours later. For subcutaneous tumor studies, $1.5 \times 10^6$ Gli36ΔEGFR or $1 \times 10^6$ U87ΔEGFR-Luc cells were implanted in the rear flanks of athymic nude mice. When Gli36ΔEGFR tumors reached 100-200 $mm^3$, they were treated with five consecutive daily doses of SapC-DOPS (SapC 13 mg/kg, DOPS 8 mg/kg) or DOPS (8 mg/kg) by tail vein injection. When U87ΔEGFR-Luc tumors reached 1,500 $mm^3$, mice were treated with a single dose of SapC-DOPS-CVM (SapC 3.2 mg/kg, DOPS 1.8 mg/kg, CVM 1.6 µmol/l). Tumors were excised 24 hours following the final treatment and harvested for immunohistochemistry analysis.

For the immunohistochemistry and immunofluorescence analysis, subcutaneous tumors and mouse brains were fixed in 4% buffered paraformaldehyde followed by 30% sucrose at 4° C., embedded in optimal-cutting temperature, and frozen at −80° C. Subcutaneous tumors were divided into 2-4 pieces, and 10-µm sections from each piece were stained with anti-CD31 (BD Pharmingen, San Jose, Calif.). The three most vascularized areas within the tumor were chosen at low magnification, and vessels were counted in a representative high magnification field in each view with n=4 tumors/group. Mouse brains bearing intracranial tumors were sectioned at 5 µm and stained using the following antibodies: anti-CD31, anti-His (GeneScript, Piscataway, N.J.), anti-cleaved caspase-3 (Cell Signaling, Danvers, Mass.), Alexa Fluor 594 (Invitrogen), and Alex Fluor 488 (Invitrogen).

All mouse experiments and care were approved by the Institutional Animal Care and Use committee of The Ohio State University. Mut3 (GFAP-cre; Nf1$^{loxP/+}$; Trp53$^{-/+}$) male mice were bred with Trp53$^{loxP/loxP}$; Pten$^{loxP/loxP}$ females to generate Mut6 mice (GFAP-cre; Nf1$^{loxP/+}$;

Trp53$^{-/loxP}$; Pten$^{loxP/+}$). Mut3 mice were maintained in B6CBAF1/J strain by breeding male Mut3 mice with female B6CBAF1/J females (the Jackson Laboratory, Bar Harbor, Me.). The mice were genotyped between p9 and P12, and the genotypes were confirmed after harvesting their tissues. Quadruple conditional knockout mice were derived by breeding GFAP-CreER; Pten$^{loxP/loxP}$; Trp53$^{loxP/loxP}$; Rb1$^{loxP/loxP}$ mice with Rb1$^{-/-}$ mice (p107-null) to generate the four gene-targeted strain. Tumors were induced by intraperitoneal tamoxifen injections.

For the in vivo bioluminescence and fluorescence imaging, CVM (PTI Research, Exton, Pa.) in ethanol was mixed with phospholipid solvent for bath sonication preparation. CVM-labeled SapC-DOPS nanovesicles were separated from free CVM dye using a Sephadex G25 column (PD-10; Amersham Pharmacia Biotech, Piscatay, N.J.). SapC-DOPS-CVM (SapC 3.2 mg/kg, DOPS 0.656 mg/kg, CVM 320 mol/l) or CVM-labeled DOPS (DOPS 0.656 mg/kg, CVM 320 mol/l) was administered by tail vein injection into orthotropic and transgenic brain tumor-bearing mice. Real-time images were taken using an IVIS 200 Series (Clipper, Alameda, Calif.) or a Kodak FX (Carestream Health, Toronto, Ontario, Canada) imaging system. For in vitro targeting experiments, cells were treated with SapC-DOPS-CVM (SapC 33 µmol/l, DOPS 100.5 µmol/l, CVM 1.6 µmol/l) or DOPS-CVM (DOPS 100.5 µmol/l, CVM 1.6 µmol/l) and evaluated by fluorescence-activated cell sorting analysis. For PtdSer-blocking experiments, cells were incubated in 0.4 mg/ml of Lact-C2 or β2GP1 for 30 minutes at 37° C. before injecting subcutaneously (100,000 cells) above the skull of nude mice. One hour later, mice were treated with CVM-labeled SapC-DOPS (SapC 3.2 mg/kg, DOPS 0.656 mg/kg, CVM 320 mol/l) and imaged 1 hour later as described above (n=3).

For the endothelial cell migration assays in the in vitro angiogenesis evaluation, HDMECs or HUVECs were cultured in 0% serum-containing media with SapC-DOPS (SapC 50 mol/l, DOPS 152 µmol/l), DOPS (152 µmol/l) or media alone for 30 minutes at 37° C. Cells (1×10$^6$) were plated in the upper chamber of transwell chambers (ISC BioExpress, Kaysville, Utah) with an 8 µm pore size, and complete endothelial cell media was used as a chemoattractant in the bottom chamber. The cells were allowed to migrate for 6 hours, and were then fixed and stained with 0.5% crystal violet. The migrated cells were quantified as number of cells/view field (n=3 view fields/well and four wells/group). For the tube formation assay, 40,000 HDMECs or HUVECs were cultured as above and plated on 250 µl of polymerized Matrigel (BD Biosciences, Bedford, Mass.) diluted to 75% in complete endothelial cell medium, and incubated at 37° C. Pictures of formed tubes were taken at 6 and 15 hours and viable tubes (>200 µm) were quantified by counting one ×10 microscopic view/well, and the data presented as means for four wells. Ex vivo aortic ring assay was completed by removing the full-length aorta from a Fisher-344 rat and sectioned into 1-mm long rings and polymerized in Matrigel. Rings were treated with SapC-DOPS (SapC 50 µmol/l, DOPS 152 µmol/l), DOPS (152 µmol/l) or media alone, and pictures were taken 48 hours later, n=4.

Student's t-test was used to analyze in vitro experiments. A P value of <0.05 was considered statistically significant. Kaplan-Meier curves were compared using the log-rank test using GraphPad Prism S/W (GraphPad Software, La Jolla, Calif.). All error bars represent SD.

Certain embodiments the compositions and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method to induce cell death in at least one glioblastoma cancer cell, comprising:

a) administering from about 0.55 μM to about 17.5 μM of a SapC-DOPS composition to at least one glioblastoma cancer cell; and, b) administering from about 1 nM to about 50 nM of a rapamycin compound to the at least one glioblastoma cancer cell;

the SapC-DOPS composition and rapamycin compound being present in amounts sufficient for inducing cell death in the at least one glioblastoma cancer cell;

wherein the SapC-DOPS composition comprises:

a phospholipid comprising dioleoylphosphatidylserine (DOPS);

an isolated saposin C-related polypeptide consisting of SEQ ID NO:2;

and a pharmaceutically acceptable carrier;

wherein the rapamycin compound comprises sirolimus; and, wherein the DOPS phospholipid forms a nanovesicle incorporating the saposin C-related polypeptide.

2. The method of claim 1, wherein step (a) is performed simultaneously with step (b).

3. The method of claim 1, further comprising waiting a period of time between step (a) and step (b).

4. The method of claim 1, which further comprises conducting a therapy prior to or after the administration of the SapC-DOPS composition and the rapamycin compound, wherein the therapy is selected from the group consisting of: surgery; radiation; chemotherapy; alternating electrical fields; ketogenic diet; temozolomide; bevadizumab; APG101; and stem cells.

* * * * *

UNITED STATES PATENT AND TRADEMARK OFFICE
CERTIFICATE OF CORRECTION

PATENT NO.         : 9,757,432 B2
APPLICATION NO.    : 14/442782
DATED              : September 12, 2017
INVENTOR(S)        : Balveen Kaur, Jeffrey Wojton and Xiaoyang Qi It is certified that error appears in the above-identified patent and that said Letters Patent is hereby corrected as shown below:

On the Title Page

Item (54) and in the Specification, Column 1, Lines 1-2,
"MATERIALS AND METHODS USEFUL FOR TREATING GLIOBLASTORNA"

Should read:
-- MATERIALS AND METHODS USEFUL FOR TREATING GLIOBLASTOMA --.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 2

<210> SEQ ID NO 1
<211> LENGTH: 524
<212> TYPE: PRT
<213> ORGANISM: Homo sapiens

<400> SEQUENCE: 1

Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95
```

```
Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
            115                 120                 125

Gly Glu Val Cys Ser Ala Leu Asn Leu Cys Glu Ser Leu Gln Lys His
            130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
            195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Pro Lys Glu Ile Cys Ala Leu Val Gly Phe Cys Asp
            260                 265                 270

Glu Val Lys Glu Met Pro Met Gln Thr Leu Val Pro Ala Lys Val Ala
            275                 280                 285

Ser Lys Asn Val Ile Pro Ala Leu Glu Leu Val Glu Pro Ile Lys Lys
            290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335

Glu Ile Leu Asp Ala Phe Asp Lys Met Cys Ser Lys Leu Pro Lys Ser
            340                 345                 350

Leu Ser Glu Glu Cys Gln Glu Val Val Asp Thr Tyr Gly Ser Ser Ile
            355                 360                 365

Leu Ser Ile Leu Leu Glu Glu Val Ser Pro Glu Leu Val Cys Ser Met
            370                 375                 380

Leu His Leu Cys Ser Gly Thr Arg Leu Pro Ala Leu Thr Val His Val
385                 390                 395                 400

Thr Gln Pro Lys Asp Gly Gly Phe Cys Glu Val Cys Lys Lys Leu Val
            405                 410                 415

Gly Tyr Leu Asp Arg Asn Leu Glu Lys Asn Ser Thr Lys Gln Glu Ile
            420                 425                 430

Leu Ala Ala Leu Glu Lys Gly Cys Ser Phe Leu Pro Asp Pro Tyr Gln
            435                 440                 445

Lys Gln Cys Asp Gln Phe Val Ala Glu Tyr Glu Pro Val Leu Ile Glu
            450                 455                 460

Ile Leu Val Glu Val Met Asp Pro Ser Phe Val Cys Leu Lys Ile Gly
465                 470                 475                 480

Ala Cys Pro Ser Ala His Lys Pro Leu Leu Gly Thr Glu Lys Cys Ile
            485                 490                 495

Trp Gly Pro Ser Tyr Trp Cys Gln Asn Thr Glu Thr Ala Ala Gln Cys
            500                 505                 510
```

```
Asn Ala Val Glu His Cys Lys Arg His Val Trp Asn
        515                 520

<210> SEQ ID NO 2
<211> LENGTH: 80
<212> TYPE: PRT
<213> ORGANISM: Homo sapiens

<400> SEQUENCE: 2

Ser Asp Val Tyr Cys Glu Val Cys Glu Phe Leu Val Lys Glu Val Thr
1               5                   10                  15

Lys Leu Ile Asp Asn Asn Lys Thr Glu Lys Glu Ile Leu Asp Ala Phe
            20                  25                  30

Asp Lys Met Cys Ser Lys Leu Pro Lys Ser Leu Ser Glu Glu Cys Gln
            35                  40                  45

Glu Val Val Asp Thr Tyr Gly Ser Ser Ile Leu Ser Ile Leu Leu Glu
        50                  55                  60

Glu Val Ser Pro Glu Leu Val Cys Ser Met Leu His Leu Cys Ser Gly
65                  70                  75                  80
```